US008553956B2

(12) United States Patent
Wu et al.

(10) Patent No.: US 8,553,956 B2
(45) Date of Patent: Oct. 8, 2013

(54) 3D CURRENT RECONSTRUCTION FROM 2D DENSE MCG IMAGES

(75) Inventors: Chenyu Wu, Mountain View, CA (US); Jing Xiao, Cupertino, CA (US)

(73) Assignee: Seiko Epson Corporation, Tokyo (JP)

( * ) Notice: Subject to any disclaimer, the term of this patent is extended or adjusted under 35 U.S.C. 154(b) by 158 days.

(21) Appl. No.: 13/300,353

(22) Filed: Nov. 18, 2011

(65) Prior Publication Data
US 2012/0219195 A1    Aug. 30, 2012

Related U.S. Application Data

(60) Provisional application No. 61/447,578, filed on Feb. 28, 2011.

(51) Int. Cl.
*G06K 9/00*    (2006.01)
*A61B 5/05*    (2006.01)

(52) U.S. Cl.
USPC ............................ 382/128; 600/407; 600/409

(58) Field of Classification Search
USPC ........ 382/100, 128, 520; 600/2, 13, 407, 409, 600/410, 425, 513, 524; 324/144, 200, 213, 324/219, 240, 263, 313, 381, 463, 529, 324/750.12
See application file for complete search history.

(56) References Cited

U.S. PATENT DOCUMENTS 5,211,178 A * 5/1993 Kado et al. ..................... 600/513
7,668,581 B2 * 2/2010 Kandori et al. ............... 600/407

OTHER PUBLICATIONS

Shulga, S., et al., "Analytical Method for Solving Inverse Problem in Magnetocardiology", Antenna Theory and Techniques, 2003. 4th International Conference, pp. 830-833, vol. 12, Sep. 2003.
Fenici, R., et al., "Magnetocardiography provides non-invasive three-dimensional electroanatomical imaging of cardiac electrophysiology", Anatolian Journal of Cardiology, 2007, 7-23-28.
Voytovych, I., et al., "Multi-Channel Magnetocardiograph: Control and Software", IEEE International Workshop on Intelligent Data Acquisition and Advanced Computing Systems, Technology and Applications, Sep. 8-10, 2003.
Bin, U., et al., "Magnetocardiographic Pattern Analysis of Re-Entry Wave Propagation in Three-Dimensional Ventricular Tissue by Using a Human Cardiac Cell Model", Journal of the Korean Physical Society, vol. 50, No. 1, Jan. 2007.

* cited by examiner

*Primary Examiner* — Abolfazl Tabatabai

(57) ABSTRACT

A current dipole is determined by solving the inverse problem multiple times in consecutive stages. At each stage, a new high resolution image is generated from a magnetic field map from the immediately previous stage, and at each stage more constraints are extracted from the current high resolution image than were available in the immediately previous stage. After the constraints are extracted from a current high resolution image, the current high resolution is updated to incorporate constraints from the immediately previous stage. The updated high resolution image, and the currently extracted constraints are used to resolve the inverse problem, and the Biot-Savart law is used to calculated the current dipole.

20 Claims, 22 Drawing Sheets

$$\vec{B}(\vec{r_m}) = \frac{\mu_0}{4\pi} \frac{\vec{J}(\vec{p}) \times (\vec{r_m} - \vec{p})}{\|\vec{r_m} - \vec{p}\|^3}, m = 1 \cdots M \qquad Eq.\ 1$$

$$B_z(\vec{r_m}) = \frac{\mu_0}{4\pi} \frac{[-J^2, J^1] \cdot [r_m^1 - x_p, r_m^2 - y_p]'}{[(r_m^1 - x_p)^2 + (r_m^2 - y_p)^2 + (r_m^3 - z_p)^2]^{3/2}} \qquad Eq.\ 2$$

$$B_z^m(z) = \frac{a_m}{[b_m + (c - z)^2]^{3/2}} \qquad Eq.\ 3$$

$$B_z^m(z + \Delta z)$$
$$= B_z^m(z) + \frac{d}{dz} B_z^m(z) \cdot \Delta z + \frac{d^2}{2dz} B_z^m(z) \cdot \Delta z^2 + O(\Delta z^3) \qquad Eq.\ 4$$

$$B_{xy}(i, j) = \sqrt{(\partial B_z(i, j)/\partial x)^2 + (\partial B_z(i, j)/\partial y)^2} \qquad Eq.\ 5$$

$$\vec{B^m} = \vec{J} \times \vec{R_m} = -\vec{R_m} \times \vec{J} \qquad Eq.\ 6$$

where $\vec{B^m} = \vec{B}(\vec{r_m})$, $\vec{J} = \vec{J}(\vec{p})$ and $\vec{R_m} = \frac{\mu_0}{4\pi} \frac{(\vec{r_m} - \vec{p})}{\|\vec{r_m} - \vec{p}\|^3}$.

FIG. 10A

$$\vec{B^m} = -[\vec{R_m}]_\times \vec{J}$$

$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix} \qquad Eq.\ 7$$

$$B_z^m = \begin{bmatrix} R_m^2, & -R_m^1 \end{bmatrix} \cdot \begin{bmatrix} J^1, & J^2 \end{bmatrix}' \qquad Eq.\ 8$$

$$\underbrace{\begin{bmatrix} B_z^1 \\ B_z^2 \\ \vdots \\ B_z^M \end{bmatrix}}_{\mathbf{B}} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{\mathbf{R}} \cdot \underbrace{\begin{bmatrix} J^1 \\ J^2 \end{bmatrix}}_{\mathbf{J}} \qquad Eq.\ 9$$

$$\mathbf{J} = (\mathbf{R}^T \mathbf{R})^{-1} \mathbf{R}^T \mathbf{B} \qquad Eq.\ 10$$

$$\vec{B^m} = \frac{\mu_0}{4\pi} \frac{\vec{J} \times ((\vec{r_0} + \vec{\delta_m}) - \vec{p})}{\|(\vec{r_0} + \vec{\delta_m}) - \vec{p}\|^3} = \frac{\mu_0}{4\pi} \frac{\vec{J} \times (\vec{\epsilon_0} + \vec{\delta_m})}{\|\vec{\epsilon_0} + \vec{\delta_m}\|^3} \qquad Eq.\ 11$$

FIG. 10B

$$\alpha \vec{B^m} = \frac{\vec{J} \times \vec{\epsilon_0} + \vec{J} \times \vec{\delta_m}}{\|\vec{\epsilon_0} + \vec{\delta_m}\|^3} \qquad Eq.\ 12$$

$$\alpha B_z^m + \frac{-J^2 x_\epsilon + J^1 y_\epsilon + \tau_m^3}{((x_\epsilon + \delta_m^1)^2 + (y_\epsilon + \delta_m^2)^2 + (z_\epsilon + \delta_m^3)^2)^{3/2}} \qquad Eq.\ 13$$
$$= f^m(x_\epsilon, y_\epsilon, z_\epsilon) = 0$$

$$z = d/\sqrt{2},\ \|\vec{J}\| = \frac{4\pi d^2 B_z^{max}}{0.385 \mu_0} \qquad Eq.\ 14$$

$$\vec{B}(\vec{r_m}) = \frac{\mu_0}{4\pi} \frac{\vec{J}(\vec{p}) \times (\vec{r_m} - \vec{p})}{\|\vec{r_m} - \vec{p}\|^3}, m = 1 \cdots M^2 \quad \text{Eq. 15}$$

$$\vec{B}(\vec{r_m}) = \vec{J}(\vec{p}) \times \vec{R_m} = -\vec{R_m} \times \vec{J}(\vec{p}) \quad \text{Eq. 16}$$

$$\vec{B^m} = -[\vec{R_m}]_\times \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix} \quad \text{Eq. 17}$$

$$B_z^m = \frac{\mu_0}{4\pi} \frac{[r_m^1 - x_p, r_m^2 - y_p] \cdot [-J^2, J^1]'}{[(r_m^1 - x_p)^2 + (r_m^2 - y_p)^2 + (r_m^3 - z_p)^2]^{3/2}} \quad \text{Eq. 18}$$

$$B_z^m(z) = \frac{a_m}{[b_m + (c-z)^2]^{3/2}} \quad \text{Eq. 19}$$

$$B_z^m(z+\delta z) = B_z^m(z) + \frac{dB_z^m(z)}{dz}\delta z + \frac{d^2 B_z^m(z)}{2dz^2}\delta z^2 + O(\delta z^3) \quad \text{Eq. 20}$$

$$\frac{d^2 B_z^m(z)}{dz^2} = \frac{\mu_0}{4\pi} \frac{a_m(12(c-z)^2 - 3b_m)}{[b_m + (c-z)^2]^{7/2}} \quad \text{Eq. 21}$$

FIG. 19b

$$\kappa = \frac{\frac{d^2 B_z^m(z)}{dz^2}}{B_z^m(z)} = \frac{12(c-z)^2 - 3b_m}{[b_m + (c-z)^2]^2} \qquad Eq.\ 22$$

$$B_{xy}(i,j) = \sqrt{(\partial B_z(i,j)/\partial x)^2 + (\partial B_z(i,j)/\partial y)^2} \qquad Eq.\ 23$$

$$z = d/\sqrt{2}, \|\vec{J}\| = \frac{4\pi d^2 B_z^{max}}{0.385 \mu_0} \qquad Eq.\ 24$$

$$\underbrace{\begin{bmatrix} B_z(1) \\ B_z(2) \\ \vdots \\ B_z(M^2) \end{bmatrix}}_{B} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{R} \cdot \underbrace{\begin{bmatrix} J^1 \\ J^2 \end{bmatrix}}_{J} \qquad Eq.\ 25$$

$$J = (R^T R)^{-1} R^T B \qquad Eq.\ 26$$

$$-\alpha B_z(m) + \frac{\mu_0}{4\pi} \cdot \frac{-J^2 \cdot (r_m^1 - x_p) + J^1 \cdot (r_m^2 - y_p)}{[(r_m^1 - x_p)^2 + (r_m^2 - y_p)^2 + (r_m^3 - z_p)^2]^{3/2}} \qquad Eq.\ 27$$

$$= f^m(x_p, y_p, z_p) = 0$$

Table 1. 3D Current Localization Error $\sqrt{(x_p - x_g)^2 + (y_p - y_g)^2 + (z_p - z_g)^2} \cdot \eta = \|B_3(m)\|$

| Number of $B_3$ Constraints | Gaussian Distribution Noise $G(0, \sigma)$ | | |
|---|---|---|---|
| | $\sigma = 5\% \cdot \eta$ | $\sigma = 10\% \cdot \eta$ | $\sigma = 15\% \cdot \eta$ |
| 8 × 8 | 0.89 +/- 0.62 mm | 2.18 +/- 1.68 mm | 2.94 +/- 2.03 mm |
| 15 × 15 | 0.88 +/- 0.63 mm | 2.12 +/- 1.72 mm | 2.93 +/- 2.03 mm |
| 36 × 36 | 0.86 +/- 0.66 mm | 2.06 +/- 1.86 mm | 2.91 +/- 2.03 mm |

| Number of $B_3$ Constraints | Uniform Distribution Noise $(0, \sigma)$ | | |
|---|---|---|---|
| | $\sigma = 5\% \cdot \eta$ | $\sigma = 10\% \cdot \eta$ | $\sigma = 15\% \cdot \eta$ |
| 8 × 8 | 0.73 +/- 0.51 mm | 1.51 +/- 1.05 mm | 2.27 +/- 2.08 mm |
| 15 × 15 | 0.72 +/- 0.51 mm | 1.50 +/- 1.05 mm | 2.26 +/- 2.08 mm |
| 36 × 36 | 0.71 +/- 0.50 mm | 1.49 +/- 1.04 mm | 2.26 +/- 2.08 mm |

FIG. 22

Table 2. Current Moment Reconstruction Error: Magnitude $\frac{\|\vec{J}_{rec}\| - \|\vec{J}_g\|}{\|\vec{J}_g\|}$, $\eta = \|B_z(m)\|$

| Noise | $\sigma = 5\% \cdot \eta$ | $\sigma = 10\% \cdot \eta$ | $\sigma = 15\% \cdot \eta$ |
|---|---|---|---|
| Gaussian Distribution $G(0, \sigma)$ | 1.5% +/- 1.4% | 3.4% +/- 2.7% | 4.3% +/- 3.6% |
| Uniform Distribution $(0, \sigma)$ | 1.1% +/- 1.1% | 2.7% +/- 2.8% | 3.4% +/- 3.4% |

FIG. 23

Table 3. Current Moment Reconstruction Error: Direction $|atan2(x_r, y_r) - atan2(x_g, y_g)|$, $\eta = \|B_z(m)\|$

| Noise | $\sigma = 5\% \cdot \eta$ | $\sigma = 10\% \cdot \eta$ | $\sigma = 15\% \cdot \eta$ |
|---|---|---|---|
| Gaussian Distribution $G(0, \sigma)$ | 0.08° +/- 0.07° | 0.16° +/- 0.15° | 0.25° +/- 0.22° |
| Uniform Distribution $(0, \sigma)$ | 0.11° +/- 0.09° | 0.21° +/- 0.17° | 0.31° +/- 0.25° |

FIG. 24

3D CURRENT RECONSTRUCTION FROM 2D DENSE MCG IMAGES

CROSS-REFERENCE TO RELATED APPLICATION(S)

This application claims the benefit of U.S. Provisional Application No. 61/447,578 filed on Feb. 28, 2011 under 35 U.S.C. §119(e) and is hereby incorporated by reference in its entirety.

BACKGROUND

1. Field of Invention

The present invention relates to the calculation of a current dipole from magnetic field measurements. More precisely, the present invention relates to improving the resolution of the inverse problem by defining more constraints than are available from the physically measured magnetic field.

2. Description of Related Art

Electric current source estimation is a common problem in various electromagnetic imaging technologies. For example, living organisms generate electric impulses, or electric fields, and electric imaging makes it possible to generate images of these electric fields. Electric imaging has found wide application in the medical field.

From physics, it is known that electric currents generate magnetic fields. Thus, organisms that generate electric impulses consequently also generate magnetic fields. The study of such magnetic fields in living organisms, or living tissues, is generally known as biomagnetism. The field of biomagnetism has been applied to the creation of magnetic images of the human brain and human heart.

The development of electric and magnetic imaging (or recording) technology permits the detection and analysis of electrophysiological processes in the brain, heart and other nerve systems. Recording/imaging of the electromagnetic fields from such tissues is typically accomplished by placing multiple electric or magnetic sensors around the tissue being studied. For example, electroencephalography (EEG) uses electric sensors placed around the brain to record electric images of brain tissue, and electrocardiography (ECG or EKG) uses electric sensors placed over the chest to record electric images of heart tissue. Similarly, magnetoencephalography (MEG) uses magnetic sensors placed around the brain to record magnetic images of brain tissue, and magnetocardiography (MCG) uses magnetic sensors placed over the chest to record magnetic images of heart tissue. Examples of an MEG unit and an MCG unit are provided in FIGS. 1A and 1B, respectively.

With reference to FIG. 1A, an MEG system consists of a large number (usually 300 or less) of magnetic sensors arranged in a spherical shape (to be fitted around a human head) to provide a high spatial resolution for measurements. The MEG system measures magnetic fields created by brain nerve activity. Each magnetic sensor measures a one-dimensional (1D) magnetic waveform, Bz, in the radial direction.

With reference to FIG. 1B, an MCG system may include a small number (normally 64 or fewer) of magnetic sensors (i.e. Superconducting Quantum Interference Devices, or SQUID arranged as a sensor planar array). Each SQUID sensor measures a 1D magnetic waveform (Bz) in the z direction, as illustrated by (x, y, z) axes. The MCG device is usually placed above and within 10 cm of a patient's chest in a location over the patient's heart. Electric current (i.e. electric impulse(s)) in the heart generates a magnetic field B that emanates out from the patient's torso. Each SQUID sensor measure the z-component (i.e. Bz) of the emanating magnetic field B that reaches it. That is, each SQUID sensor measures a 1D magnetic waveform in the z direction.

Compared to electric imaging (or recording) technology such as EEG and ECG, magnetic imaging technology such as MEG and MCG would be preferred due it being more noninvasive and providing a 2D image (by virtual of the x-y plane of SQUID sensors) at each time point. Moreover, the magnetic field generated outside of the human body is not distorted in the direction perpendicular to the body surface (e.g. the radial direction in FIG. 1A and the z-direction in FIG. 1B), due to the magnetic property of body tissue. Thus magnetic imaging is more accurate and sensitive to weak electric activity within the body.

By way of example, the following discussion focuses on magnetic imaging of heart tissue, but it is to be understood that the following discussion is also generally applicable to magnetic imaging and in particular applicable to magnetic imaging of other living tissues.

Cardiac electric currents (or current impulses) are generated by electrophysiological processes in the heart. Localization of abnormal electric currents may be used in the diagnosing of ischemic diseases such as myocardial infarction, angina cordis, etc. It also benefits patients in the catheter lab for both treatment and follow-up, as is explained in "Forty Years of Magnetocardiology", by F. Stroink, in Int. Conf. on Biomagnetism Advances in Biomagnetism, 28:1-8, 2010.

Traditionally, irregular cardiac electric activity, such as arrhythmia, is diagnosed by means of an electrocardiogram (ECG). However, an ECG only provides temporal information, and thus cannot localize abnormal electric impulse currents in the heart directly, even if the ischemic disease has been detected. One technique to attempt to localize electrical impulse currents is known as Body Surface Potential Mapping (BSPM), which uses a large number of electrodes (i.e., leads) to reconstruct a body surface potential map. This BSPM technique is explained in "Noninvasive Volumetric Imaging of Cardiac Electrophysiology", by Wang et al., in CVPR, pages 2176-2183, 2009. The accuracy of BSPM electric current localization, however, is limited because the observed electrical signals can be distorted by the poor conductivity of body tissue.

The advent of the magnetocardiogram, or magnetocardiography, (MCG) made available more accurate measurements of cardiac electric impulse currents, both spatially and temporally. An MCG is described above in reference to FIG. 1B.

In an MCG system, electromagnetic sensors (i.e. SQUID sensor) are arranged as a sensor planar array. Each electromagnetic sensor is a capture point, and hereinafter may be referred to as a "capture". Each capture measures a one-dimensional (i.e. 1D) magnetic waveform in a direction perpendicular to the sensor planar array (i.e. the z-direction) emanating from the patient's chest (i.e. human torso). By aligning (or synchronizing) the depth measures (i.e. the 1D magnetic waveform) of the planar array of captures at a given depth in the z-direction (which may define an observation plane through the heart tissue), a two-dimensional (2D) MCG map at the given depth may be constructed. The MCG system is usually placed five to ten centimeters above the patient's chest 21, and measures the patient's heart magnetic field in a non-invasive manner. Thus, the array of captures measure a collection of low resolution (hereinafter, low-res), two-dimensional (2D) MCG maps of electromagnetic activity.

MCG has a few advantages over ECG. First, the magnetic field generated by the heart's electric current impulses (hereinafter, currents, electric currents or electrical currents) is not distorted in the direction perpendicular to the body surface (i.e., the z direction), due to the magnetic property of body tissue. Thus MCG is more accurate and sensitive to weak electric activity in the early stage of heart disorders. Second, the MCG sensor array can localize the position of electric currents in the heart. Finally, MCG measurements are non-invasive. After forty years of research in MCG, cardiac electric current localization and high resolution visualization for MCG measurements are attracting more and more interest from both research and clinical areas.

However, there are a number of difficulties associated with MCG. A first difficulty is the great amount of electromagnetic noise that can obscure the small magnetic fields created in a human heart. This has been addressed, to some extent, by using a magnetically-shielded room to reduce background noise and by the introduction of a sensitive electromagnetic sensor 13, such as the superconducting quantum interference device (SQUID). Although these steps have helped, the raw readings nonetheless remain more noisy than desired.

Another difficulty is the limited number of electromagnetic sensors (i.e. SQUIDs) that may be used in an MCG system, which limits the resolution of an MCG map. As a result, the MCG system can typically produce only low resolution (low-res) 2D MCG maps. Typically, these low-res 2D MCG maps are not sufficient for localizing electric currents in the heart. For example, a 64 channel Hitachi™ MCG system with a 25 mm sensor interval (as described in "Newly Developed Magnetocardiographic System for Diagnosing Heart Disease", by Tsukada et al., in *Hitachi Review,* 50(1):13-17, 2001) only measures an 8×8 MCG map (i.e. an 8×8 array of 64 measurement points, or captures). One solution is to increase the number of sensors, but this is very difficult in practice due to the physical size of the sensors and system design.

An alternate approach is to approximate a high-res magnetic image from the low-res image created by the limited number of magnetic sensors. Thus, a necessary step in MCG is generating a high resolution (hereinafter high-res) 2D MCG image, or map, from a low-res 2D MCG image, or map. Two image examples L and R of high-res 2D MCG images are shown in FIG. 2. Left image L shows the tangential image of a generated high-res MCG image of a healthy heart. The maximal point (i.e. strongest point) within image L indicates the location (or source) of electric current in the heart. Thus, high-res MCG images permits doctors to directly "see" the electrical activity in the heart. Right image R shows the tangential image of a high-res MCG image of an unhealthy heart. It differs significantly from left image L of a healthy heart, and thus provides important cues for diagnosis. Compared to low-res MCG maps, high-res MCG images provide more diagnostic significance, and serve as the basis for an accurate electric current localization.

One way to generate a high-res magnetic field image from a low-res magnetic image is by interpolation. Most modern MCG systems use curve fitting interpolation methods between observed measurements of the electromagnetic sensors to construct high-res 2D MCG images from the low-res 2D MCG maps, such as described in "Magnetocardiographic Localization of Arrhythmia Substrates: A Methodology Study With Accessory Path-Way Ablation as Reference", by B. A. S. et al., in *Ann Noninvasive Electrocardiol,* 10(2):152-160, 2005, and described in "Evaluation of an Infarction Vector by Magnetocardiogram: Detection of Electromotive Forces that Cannot be Deduced from an Electrocardiogram", by Nomura et al, in *Int. Congress Series,* 1300:512-515, 2007. Unfortunately, the accuracy of curve fitting methods is typically limited.

Recently machine learning techniques have been used for high-res magnetic field image generation. An example is presented in *Interpolation in MCG Mapping*, IEEE Engineering in Medicine and Biology 27th Annual Conference, Shanghai, China, pages 4381-4384, 2005, S. Jiang et al. This approach illustrates learning nonlinear interpolation functions using neural networks.

Another approach toward generating high-res magnetic images from low-res measurement images is to make use of the inverse problem, which attempts to identify the current impulse that generated an observed magnetic image. That is, using the obtained magnetic field measurements at different sites, one attempts to estimate the location and moment of the current source that generated the observed (i.e. the measured) magnetic field. This is called the inverse problem. For example, *Conversion of Magnetocardiographic Recordings Between Two Different Multichannel Squid Devices*, IEEE Trans. on Biomedical Engineering, 47(7):869-875, 2000, by M. B. et al. describes solving the inverse problem to reconstruct the 3D position, magnitude and orientation of current sources. Once the current source is known, the high-res magnetic field can be computed from the reconstructed current source by use of the Biot-Savart law. However, due to its poor initiation, this approach is often unreliable. Nonetheless, several approaches towards addressing the inverse problem have been proposed.

However, there are a number of difficulties involved in addressing the inverse problem. According to the Helmboltz reciprocity principal, the inverse problem for MCG is an ill-posed problem unless the prior electric currents and their number is known. For example, a trivia case that assumes a single electric current located at the world origin and far from the sensor array is described in *Magnetocardiographic Localization of Arrhythmia Substrates: a Methodology Study with Accessory Pathway Ablation as Reference*, Europace, 11(2): 169-177, 2009, R. J. et al. This situation cannot be satisfied in practice.

In the case of estimating a large number of current sources, such as estimating nerve activity in the brain, the inverse problem can be put under constraints, such as describe in *Magnetic Source Images Determined by a Lead-Field Analysis The Unique Minimum-Norm Least-Squares Estimation*, IEEE Trans. Biomed Eng., 39(7):665-675, 1992, by J. Z. Wang et al. This approach requires solving a large scale non-linear optimization problem, which is often computationally expensive and may lead to undesired local optima without good initialization.

Alternatively, by considering the temporal information and signal-to-noise ratio, the inverse problem can by addressed by the beam-former and synthetic aperture magnetometery (SAM) methods, as described in *MEG Inverse Problem with Leadfieds,* 15th Japan Biomagnetism Conference, 13(1):42-45, 2000, by A. Matani. These type of methods require a statistical analysis of specific current sources, and thus does not permit the use of a one-time 2D magnetic field image without any assumptions on current sources.

Thus, addressing the inverse problem usually requires that it be simplified by making use of regularization methods (as described by Matani, above) and that the position of current sources be given by prior (as described in *An Optimal Constrained Linear Inverse Method for Magnetic Source Imaging*, Nuclear Science Symposium and Medical Imaging Conference, pages 1241-1245, 1993, by P. Hughett).

However, linear solutions to the inverse problem can be approximated in special cases where the current positions are fixed at uniform 3D grids, as put forth by J. Z. Wang et al. (cited above) and in *Simulation Studies of Biomagnetic Computed Tomography*, IEEE Trans. Biomed Eng., 40(4):317-322, 1993, C. Ramon et al.

C. Ramon et al. also show that the inverse problem can have over-constraints in the case of a single current source, which is popularly used in many applications of heart diseases diagnosis. But even in this case, the inverse problem is still a medium-scale nonlinear optimization process, which highly depends on the initialization and the number of independent constraints. However, the sparse magnetic measurement can only provide limited information for estimating good initialization and solving the inverse problem. For example, a 64-channel Hitachi MCG system only measures magnetic fields on an 8×8 grid with a 25 mm sensor interval.

What is needed is an MCG system that successfully further reduces the noise in observed low-res MCG maps.

Also needed is a method of better utilizing the high-res MCG maps to improve the observed measurements of an MCG system.

SUMMARY OF INVENTION

The above objects are met in a system for constructing a current dipole, including: a sensor unit including a plurality of electromagnetic sensors producing a sparse measurement output of data values in a direction normal to the electromagnetic sensors, the sparse measurement output constituting a first low-resolution image having a first resolution; a high resolution image synthesizer for receiving the first low resolution image and producing a first high resolution image, the first high resolution image being a higher resolution representation of the first low resolution image; a first inverse problem solver data processing block for receiving the first high resolution image and the first low resolution image and calculating a three-dimensional (3D) location and moment of the current source represented by the first high resolution image given the constraints of the first low-resolution image; a low resolution image generator receiving the calculating 3D location and moment of the current source from the first inverse problem solver data processing block, and computing an intermediate low-res image having plurality of data point positions, each corresponding to one of the sparse measurements of the plurality of electromagnetic sensors as indicated in the first low resolution image; a first image updating processing block receiving the intermediate low-res image and comparing it to the first low resolution image, wherein for each data point position in the intermediate low-res image, IF the difference between its current data value and the data value of the its corresponding sparse measurement from the first low resolution image is bigger than a predefined threshold, THEN retaining its current data value, ELSE replacing its current data value with its corresponding sparse measurement from the first low resolution image, the result being an updated intermediate low-res image; a second high resolution image synthesizer for receiving the updated intermediate low-res image and producing a second high resolution image, the second high resolution image being a higher resolution representation of the updated intermediate low-res image; a data extracting processing block for extracting data points from the second high resolution image, the extracted data points constituting an extracted field image of higher resolution than the first low-res image, the extracted field image including a subset of the extracted data values, each extracted data value in the subset corresponding to one of the sparse measurements of the plurality of electromagnetic sensors as indicated in the first low resolution image; a second image updating processing block receiving the extracted field image and replacing the subset of the extracted data values with their corresponding values in the updated intermediate low-res image, the result being an updated extracted field image; and a second inverse problem solver data processing block receiving the second high resolution image and updated extracted field image and calculating a second 3D location and moment of the current source represented by the second high resolution image given the constraints of the updated extracted field image, the current dipole being defined by the second 3D location and moment.

In the present system, the data values in the produced sparse measurement output are preferably magnetic data values.

Also in the present system, the intermediate low-resolution image is of equal resolution as the first low-resolution image and has a one-to-one data point correspondence with the first low-resolution image.

Additionally, the intermediate low-res image computed by the low resolution image generator is a magnetic field intermediate low-res image.

Predefined difference between a current data value and the data value of its corresponding sparse measurement from the first low resolution image is compared to a threshold of $0.4e^{-13}$.

In one embodiment, the first and second high resolution image synthesizers may be part of a common high resolution image synthesizing data processing block.

Also preferably, the field image extracted by the data extracting processing block is a magnetic field image.

Furthermore, the field image extracted by the data extracting processing block may be of comparable resolution as the second high resolution image.

Additionally, the first and second image updating processing blocks may be part of a common image updating processing block. Similarly, the first and second inverse problem solver data processing blocks may be part of a common inverse problem solver data processing block.

Preferably, the present system is a magnetocardiogram (MCG) system having an M×M array of the electromagnetic sensors. Alternatively, the present system may be a magnetoencephalograph (MEG) system.

The present objects further met in a method of constructing a current dipole from a real-world low-resolution (low-res) image obtained from physical magnetic sensors, including: constructing a first high resolution (high-res) image representation of the real-world low-res image, the first high-res image being of higher resolution than the real-world low-res image; estimating a first 2 dimensional (2D) location of a first estimated current source represented by the first high-res image; using the first estimated current source to initialize the inverse problem, and using the Biot-Savart law along with constraints from the real-world low-res image, computing a low-res magnetic field at a plurality of simulated sensor positions, each corresponding to one of the physical magnetic sensors, to produce a reconstructed intermediate low-res image; updating the reconstructed intermediate low-res image as follows, for each sensor position in the reconstructed intermediate low-res image, IF the difference between its current magnetic field value and the value of the its corresponding physical magnetic sensor as determine from the real-world low-res image is bigger than a predefined threshold, THEN retaining its current magnetic field value; ELSE replacing its current magnetic field value with the original corresponding value from the real-world low-res image, the result being an updated reconstructed intermediate low-res image; constructing a second high-res image representation of the updated reconstructed intermediate low-res image; second high resolution image being a higher resolution representation of the reconstructed intermediate low-res image; creating an extracted field map by extracting magnetic field values from the second high-res image, the extracted field map being of higher resolution than the real-world low-res image, the extracted field map including a subset of the extracted data values of equal resolution as the reconstructed intermediate low-res image, each extracted data value in the subset having a one-to-one correspondence with a data value in the reconstructed intermediate low-res image; within the extracted field map, replacing each extracted data value in the subset with its corresponding data value in the reconstructed intermediate low-res image, the result being an updated extracted field map; estimating a second 2D location of a second estimated current source represented by the second high-res image; using the second estimated current source to initialize the inverse problem and the updated extracted field map as constraints to the inverse problem, solve the inverse problem to define the current dipole.

In this case, the first high-res image is preferably constructed by fitting the real-world low-res image to a high-res model. Further preferably, the high-res model is built by PCA analysis of a set of randomly generated, simulated, high-res magnetic images with known current sources.

It is further preferred the second high-res image be constructed by fitting updated reconstructed low-res image to the high-res model.

The extracted field map may optionally be of comparable (or equal) resolution as the second high-res image. For example, the extracted field map and the second high-res image may both be 36×36 image maps.

The present objects are also met in a magnetoencephalograph (MEG) system implementing the method of claim 13. Similarly, the present objects may also be met in a magnetocardiogram (MCG) implementing the method of claim 13.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts.

FIGS. 10A to 10C show various equations (Eq. 1 to Eq. 12) to facilitate discussion of some aspects of the present invention.

versus depth, z.

Figure 13:
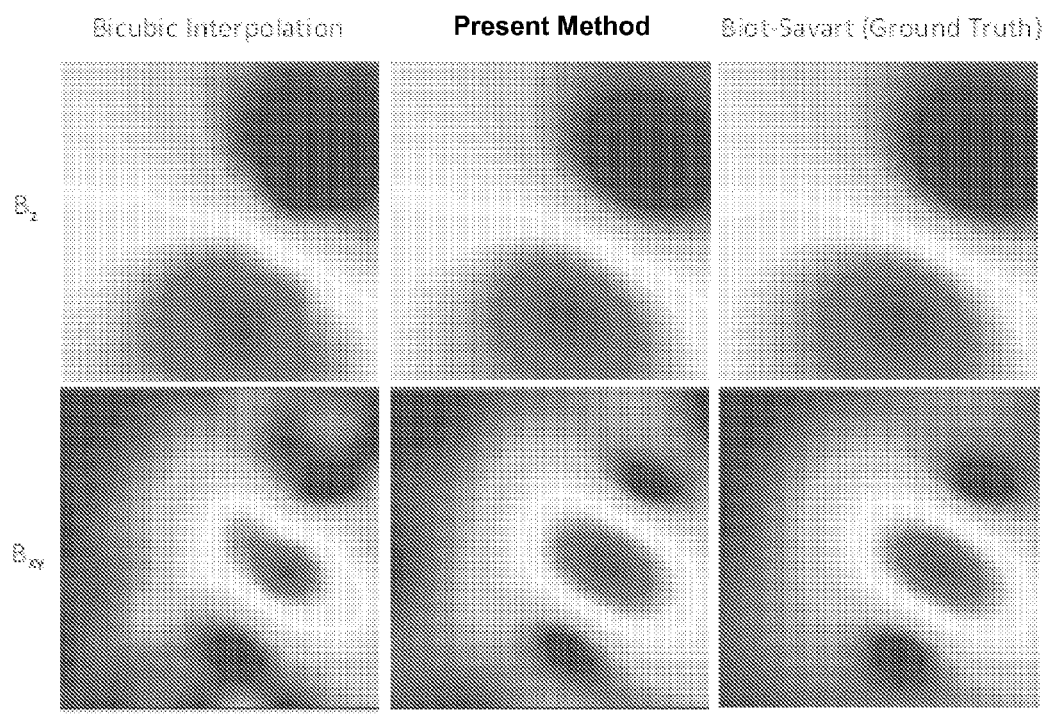

FIG. 13 compares high-res images generated by a presently preferred method and a prior art method with ground truth samples.

Figure 14:
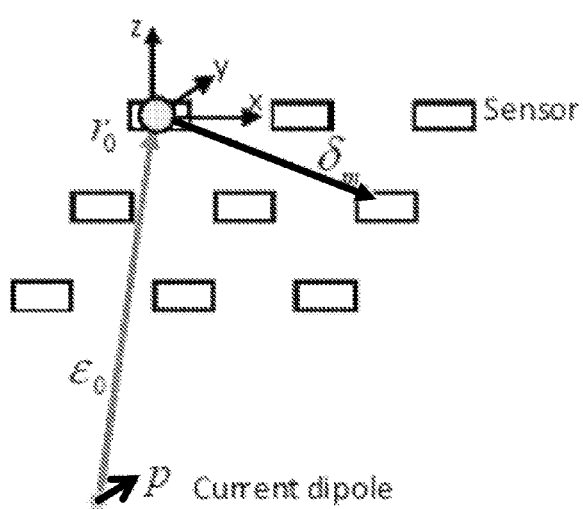

FIG. 14 illustrates a setup in the calculation of the inverse problem.

Figure 15:
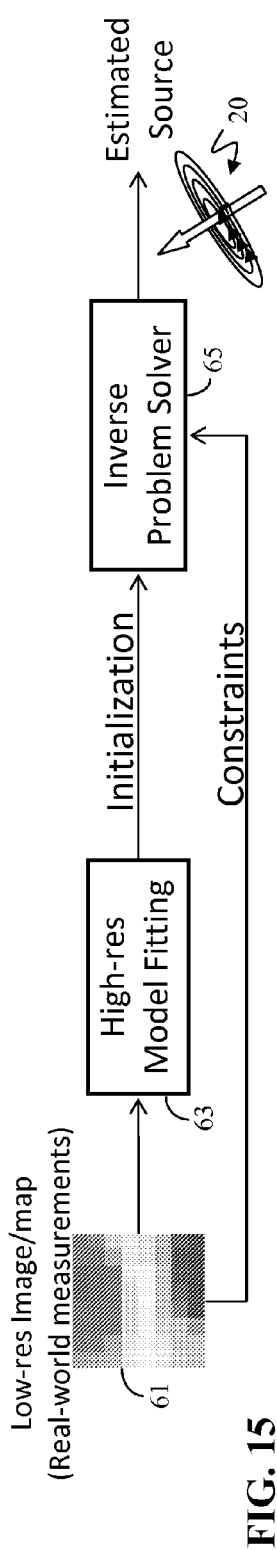

FIG. 15 is an overview of one process for resolving the inverse problem.

Figure 16:
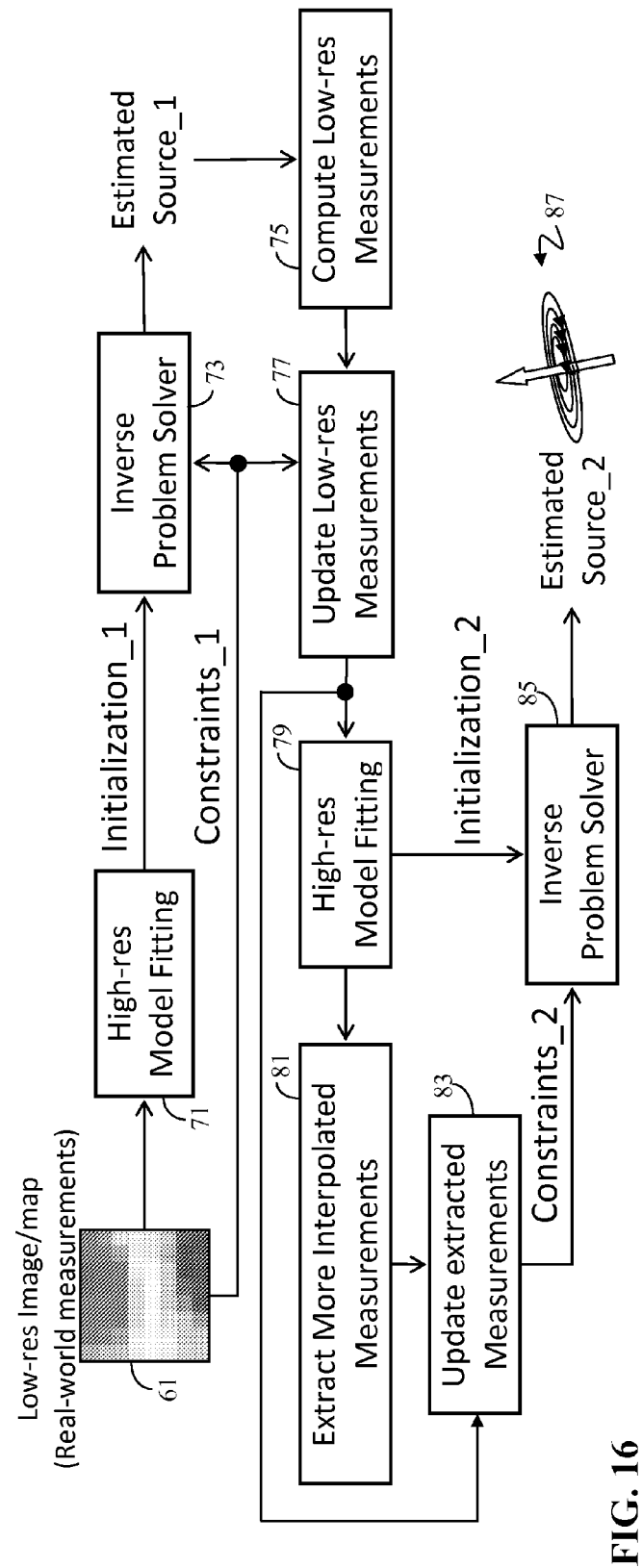

FIG. 16 is an overview of the presently preferred method/system for resolving the inverse problem.

Figure 17:
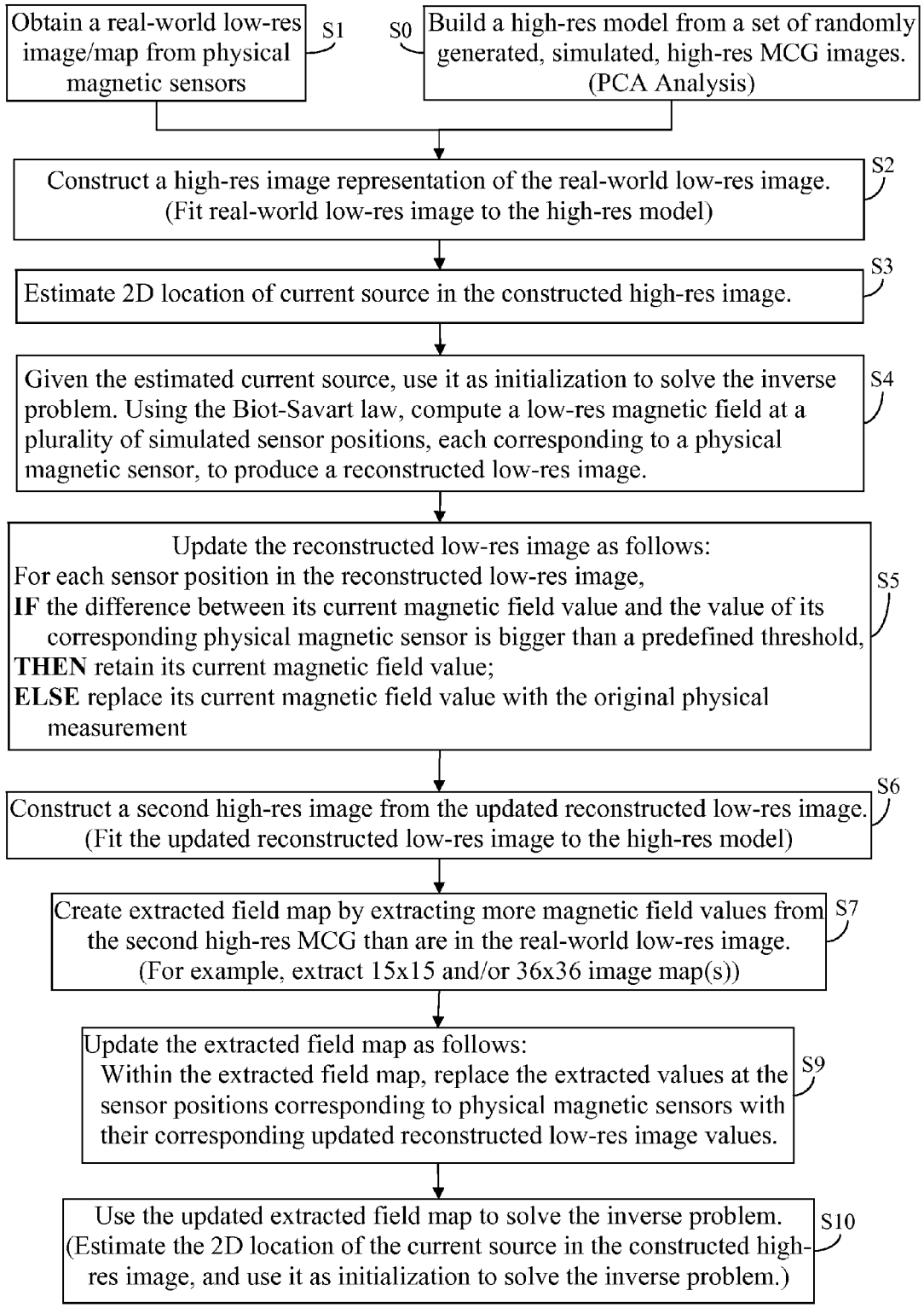

FIG. 17 is a flow chart illustrating the presently preferred method/system for resolving the inverse problem.

Figure 18C:
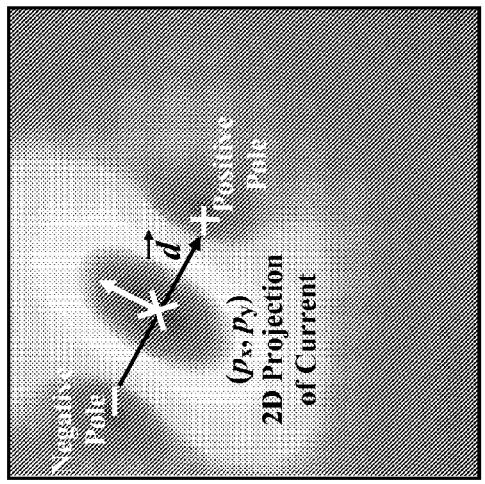
Figure 18B:
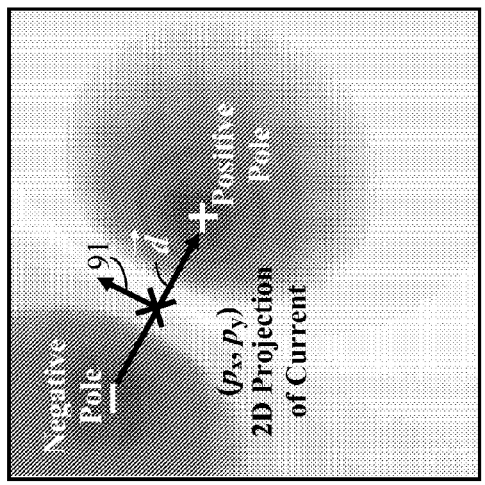
Figure 18A:
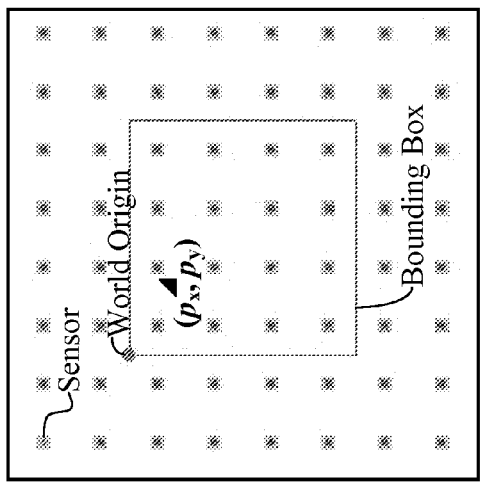

FIGS. 18a, 18b and 18c show a 2D sensor array and corresponding high-res magnetic field images.

FIGS. 19a and 19b show various equations useful in the discussing the presently preferred method of resolving the inverse problem.

Figure 20B:
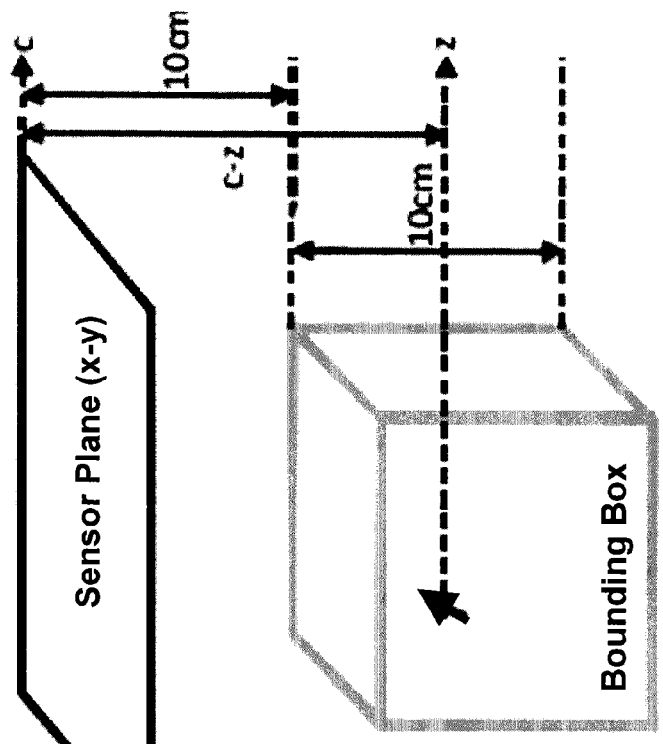
Figure 20A:
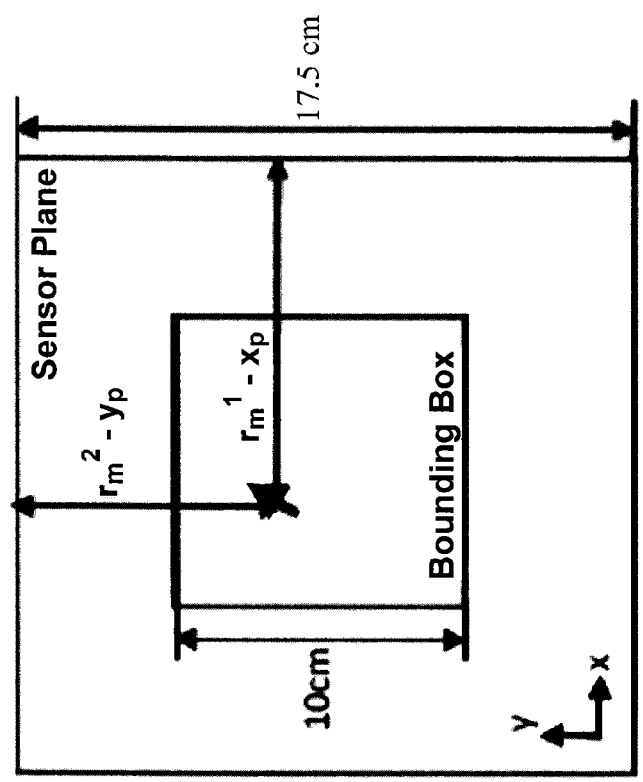

FIGS. 20a and 20b illustrate the spatial configuration of a sensor plane and bounding box in an example of the present invention.

Figure 21:
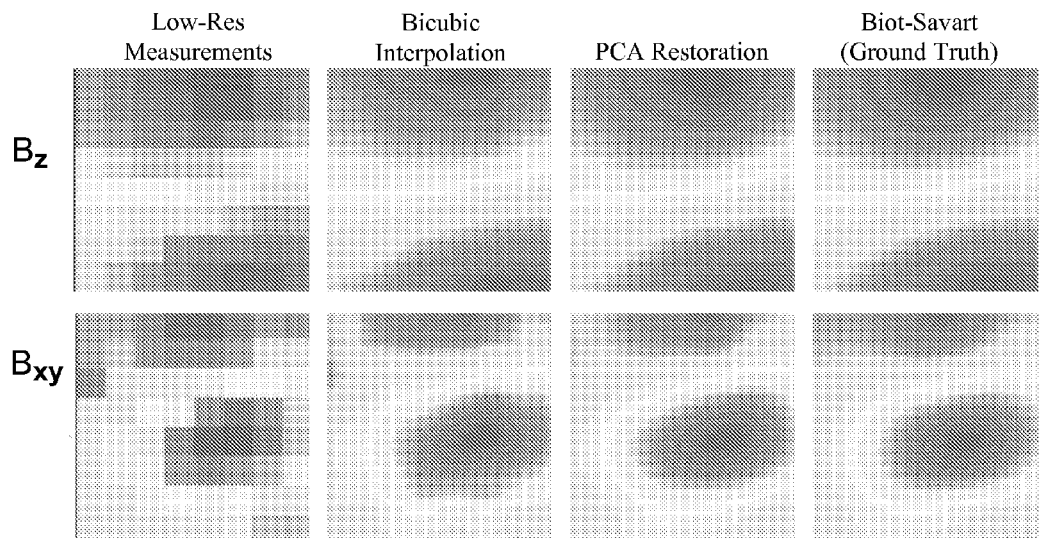

FIG. 21 shows low-res measurements (i.e. a low-res image), a high-res magnetic field image restored/created by prior art method, a high res-magnetic field image generated by the presently preferred method, and a ground truth high-res image.

FIG. 22 provides Table 1, which shows the 3D localization error resulting from the presently preferred.

FIG. 23 provides Table 2, which shows the source magnitude estimation error.

FIG. 24 provides Table 3, which shows the difference in direction between the estimated current moment $\vec{J}_{rec}$ and the true current moment.

Figure 25:
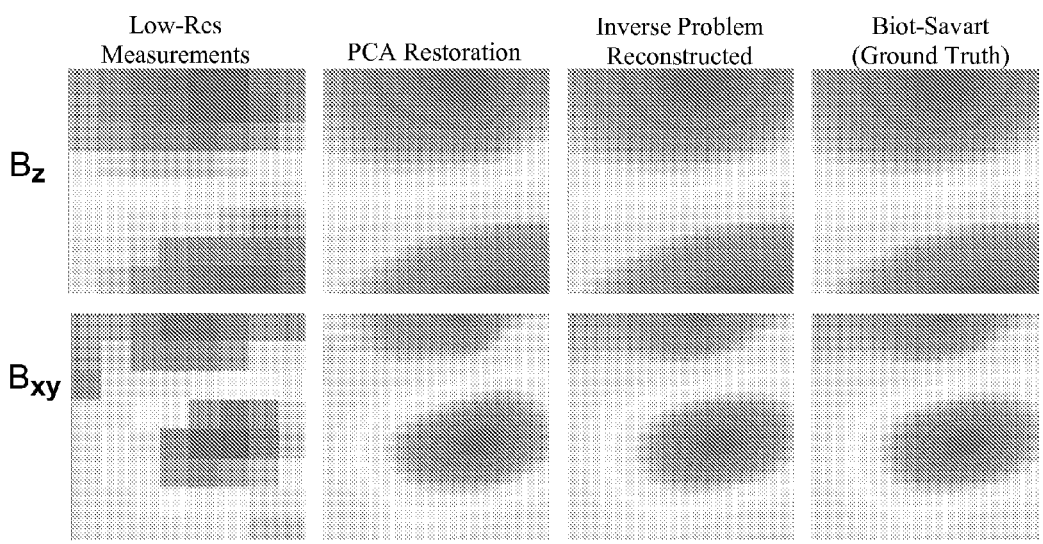

FIG. 25 shows a low-res magnetic image provided by low-res measurements, a high-res magnetic field images restored by a linear model as illustrated in FIG. 15, a high-res magnetic field computed given the reconstructed current ($\vec{J}_{rec}, \vec{p}_{rec}$) obtained by the presently preferred method as illustrated in FIG. 16, and the ground truth high-res magnetic field computed given the true current source ($\vec{J}_g, \vec{p}_g$).

Figure 26:
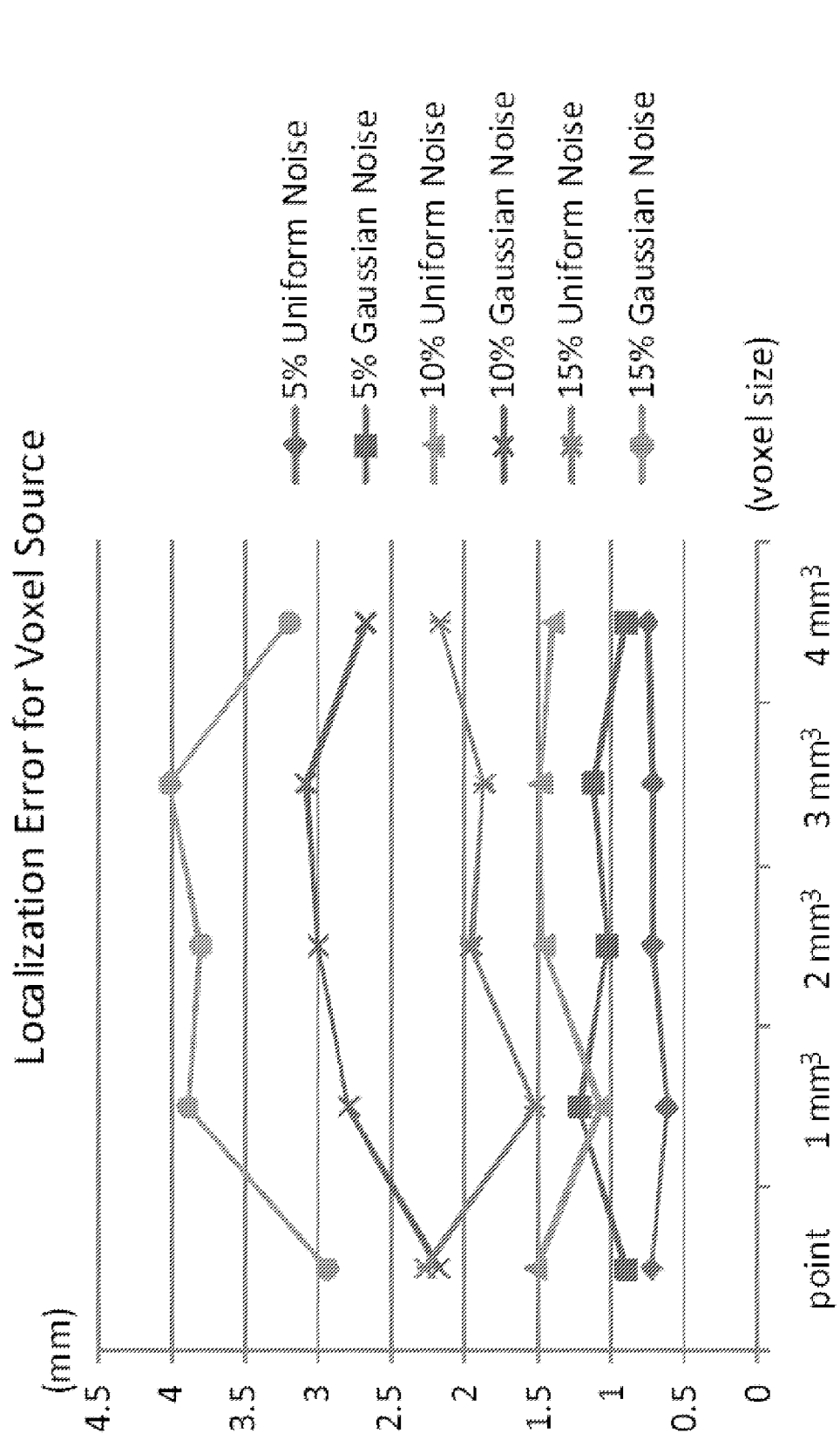

FIG. 26 shows the localization error for voxel current sources.

Figure 27:
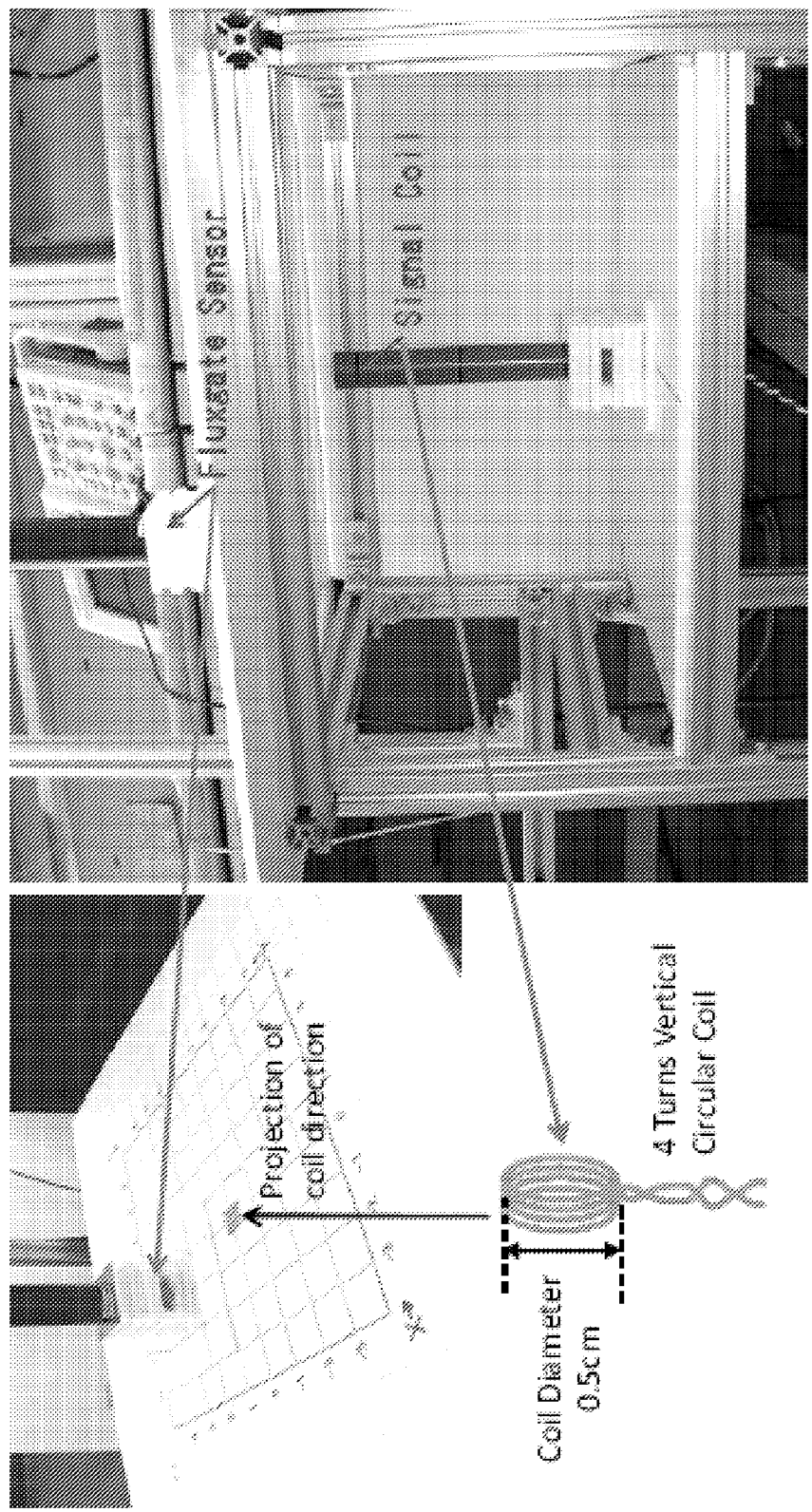

FIG. 27 illustrates a real phantom experiment.

Figure 28:
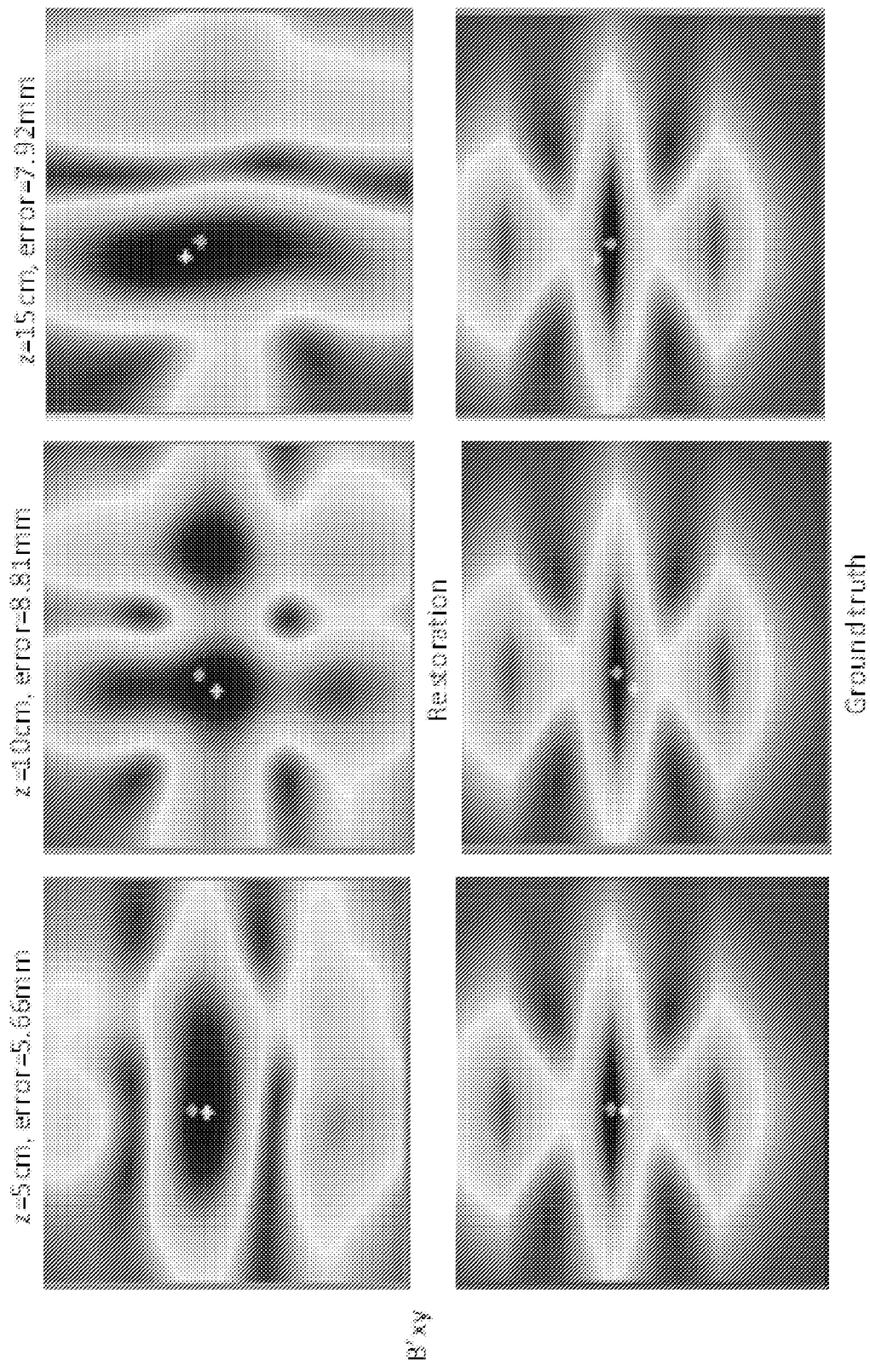

FIG. 28 illustrates different high-res images recovered at different depth levels.

DESCRIPTION OF THE PREFERRED EMBODIMENTS

Electric current source estimation is a common problem to various electric imaging and magnetic imaging technologies. Estimation of a current source is beneficial to many research areas and clinical applications. For example, estimation of the position and moment of current sources in the brain has important implications for studying neuronal populations such as functional organization of cell assemblies, and localization of abnormal electric current sources in the heart is critical for diagnosing ischemic diseases such as myocardial infarction and angina cordis. Estimation of a current source also benefits patients in the catheter lab for both treatment and follow-up, e.g. for detection of the pre-excitation path of the Wolff-Parkinson-White syndrome.

Typically, magnetic sensors are used to continuously measure in the temporal domain the z-component of a magnetic field emanating from live tissue. This results in a series of 2D magnetic field images, where each 2D magnetic field image corresponds to a specific physiology time point, such as, for example, the start of the atrial systole stage in the cardiac cycle. Using the obtained magnetic field measurements at different sites to attempt to estimate the location and moment of the current source that generated the measured magnetic field is called the inverse problem.

This estimated location and movement of the current source may be thought of as a current dipole (or flow dipole, as it might be understood) in 3D space. As it is known in the art, a flow dipole is a separation of a sink and a source. Applying this basic definition to a current dipole in a brain synapse (depending on whether the synapse is excitatory or inhibitory), the dendrite may serve as the source and the soma as the sink of the current dipole (or vise-versa).

Herein is developed an algorithm based on model learning to solve the inverse problem based on a set of sparse measurements acquired from multiple magnetic sensors, such as Superconducting Quantum Interference Device (SQUID) sensors used in magnetoencephalography (MEG) and magnetocardiography (MCG). A high resolution (i.e. high-res) magnetic field image is first estimated by fitting a linear model with the sparse measurements obtained from the magnetic sensors. Preferably, the high resolution image is distinguished from the low-resolution image by having a resolution at least 20 times greater than the resolution of the low-resolution image. The model is constructed using a library of synthesized high-res training images, which basically consists of a large number of randomly generated high-res magnetic field images based on the Biot-Savart law. Next, the 2D position of the current source is detected as the maximum in the tangential image of the estimated high-res magnetic field image. Finally, a dual-update algorithm is developed to solve the inverse problem initialized by the previous step. It is demonstrated that the restored high-res magnetic field provides more constraints to the inverse problem and helps improve the accuracy. Simulation and real experiment on a single point dipole model show that the present approach is capable of accurately estimating the location and moment of the current sources.

Before discussing the present invention in detail, it may be helpful to first describe the general structure of a typical magnetocardiographic system and describe some of the building blocks of the present invention.

Figures 1A, 1B:
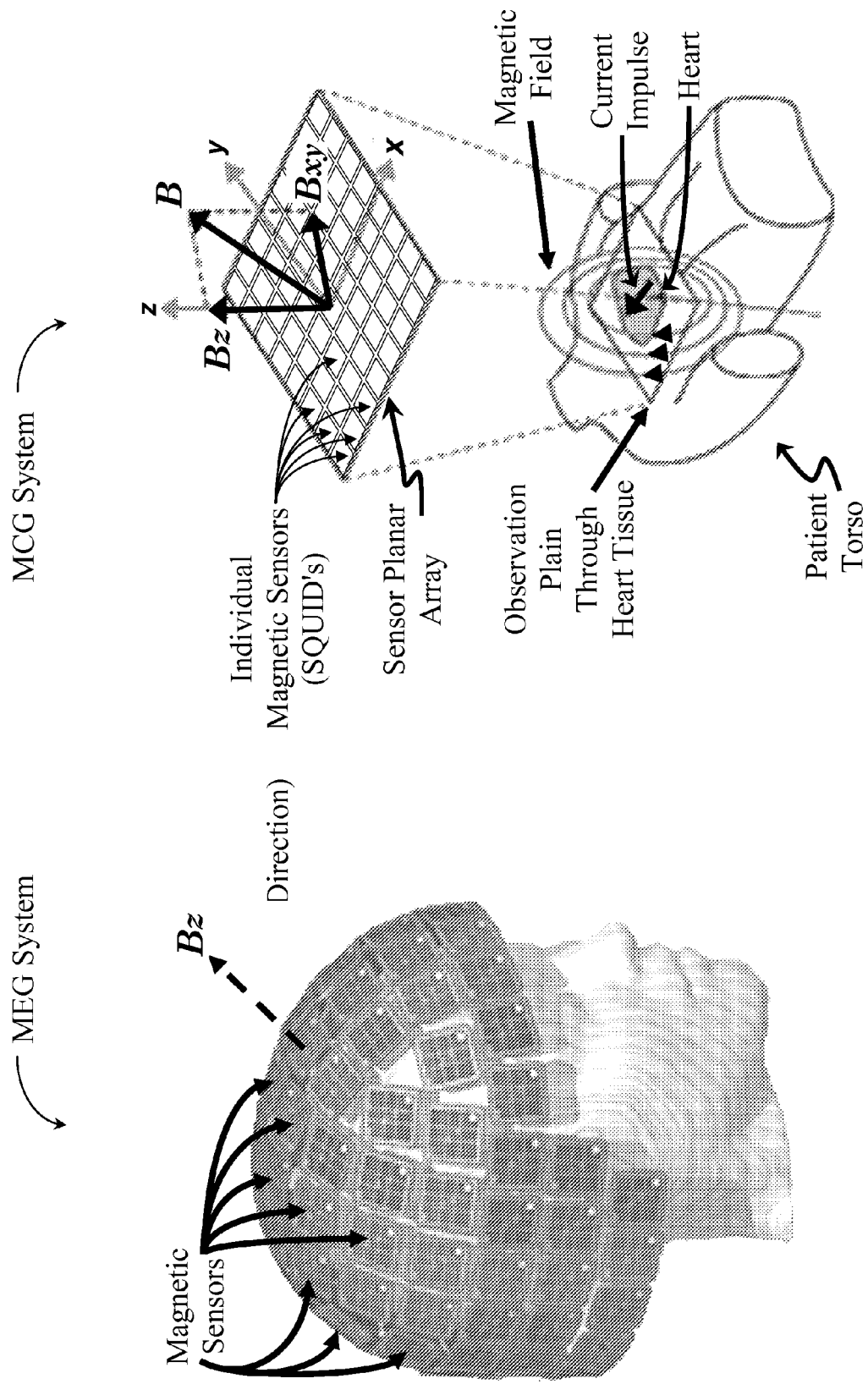
FIGS. 1A and 1B are examples of an MEG unit and an MCG unit, respectively.
Figure 2:
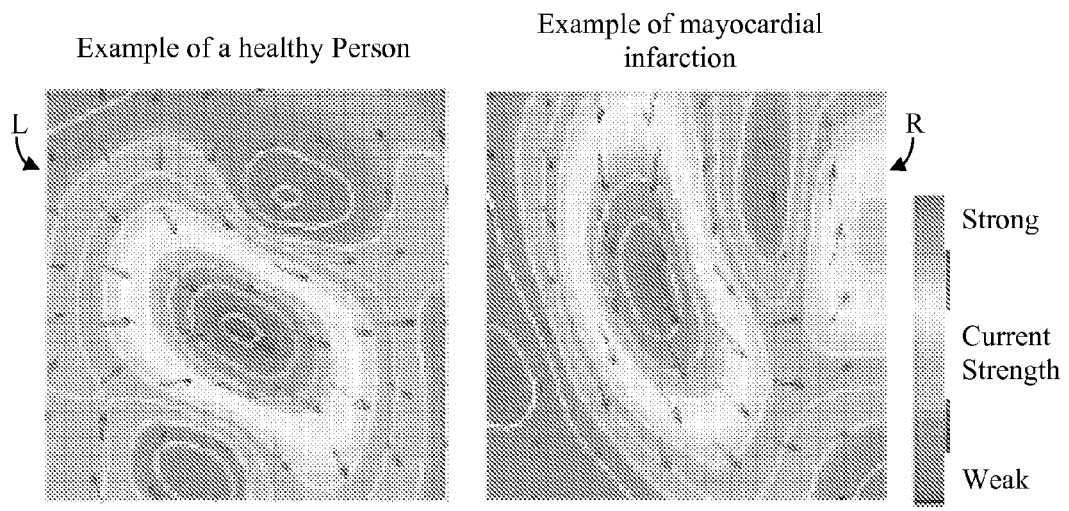
FIG. 2 shows two image examples of high-res 2D MCG images.
Figure 3:
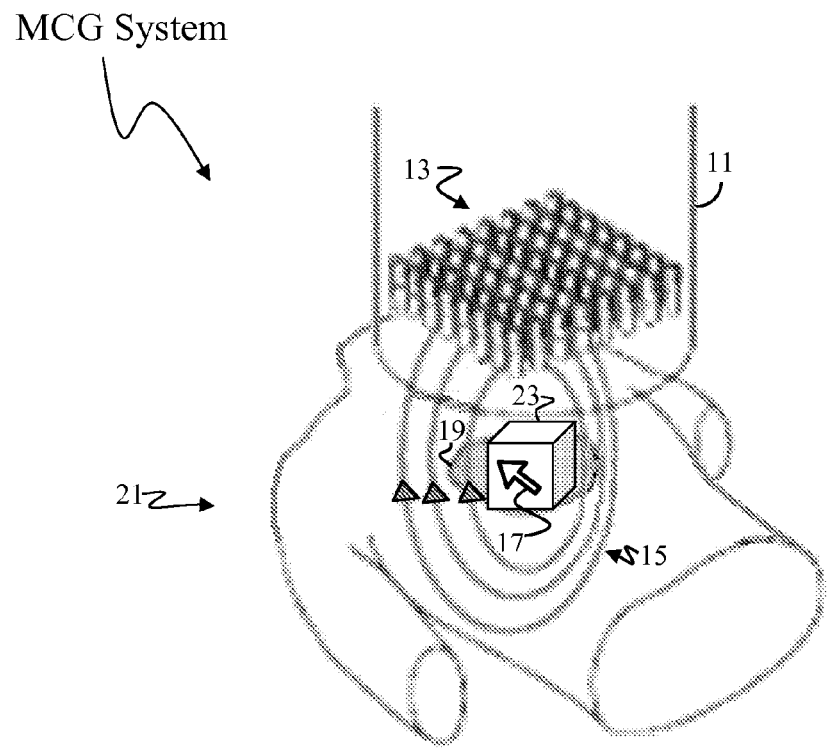
FIG. 3 illustrates an MCG system.

With reference to FIG. 3, an MCG system consists of an MCG sensor unit 11 housing a small number of individual electromagnetic sensors 13 (typically arranged as a planar array of sixty-four or fewer sensors). Electrical impulses 17 within the body create a magnetic field 15. In the present case, the human heart 19 functions as the observed source of electrical impulses 17 (i.e. as the current source).

Each electromagnetic sensor 13 is a capture point, and hereinafter may be referred to as a capture 13. Each capture 13 measures a one-dimensional (i.e. 1D) magnetic waveform in a direction perpendicular to the sensor planar array (i.e. the z-direction) emanating from the patient's chest 21 (i.e. human torso). By aligning (or synchronizing) the depth measures (i.e. the 1D magnetic waveform) of the array of captures 13 at a given depth in the z-direction, a two-dimensional (2D) MCG map at the given depth may be constructed. The MCG sensor unit 11 is usually placed five to ten centimeters above the patient's chest 21, and measures the patient's heart magnetic field in a non-invasive manner. Thus, the array of captures 13 measure a collection of low resolution (hereinafter, low-res), two-dimensional (2D) MCG maps of electromagnetic activity.

In order to better interpret the low-res, 2D MCG image maps, it is helpful to make use of a model of electrical activity in the given tissue, i.e. the human heart in the present case. Preferably, this model is a high-res model capable of receiving low-res, 2D MCG maps of electromagnetic activity, and output a simulated high-res, 2D MCG maps that correspond to the low-res, 2D maps. This may be achieved by simulating heart 19 as a block of heart tissue 23, and defining a high-res model based on block of heart tissue 23.

Figure 4:
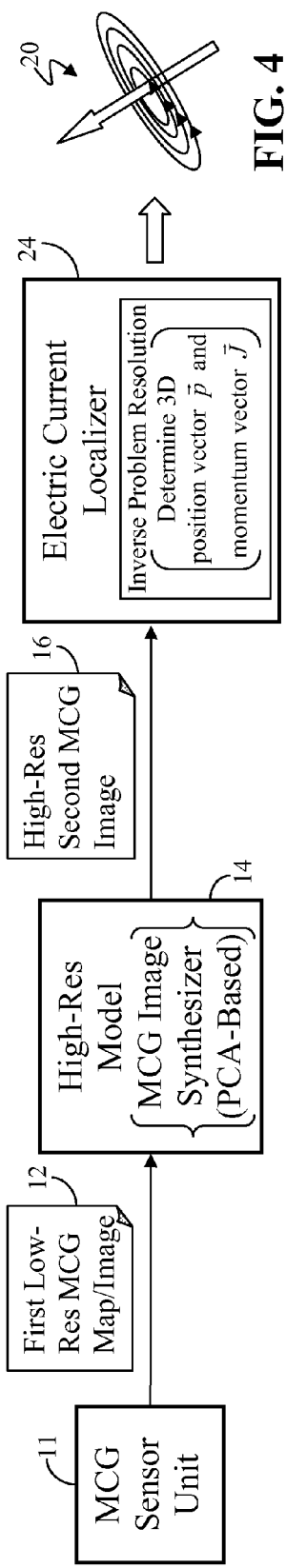
FIG. 4 illustrates a general flow of a simplified process in an MCG system that utilizes a high-res model.

A general flow of a simplified process in an MCG system that utilizes a high-res model is shown in FIG. 4. The physical MCG sensor unit 11 produces a first low-res MCG map, or image, 12, as explained above. This first low-res MCG image 12 is than passed to high-res model 14, which produces a high-res, 2D second MCG image 16. Preferably, high-res model 14 is based on a principle component analysis (PCA) of a multitude of training high-res images, as is explained in more detail below. High-res second MCG image 16 is a higher resolution image representation of first MCG image 12. For example, if first MCG image 12 has an M×M pixel resolution, then second MCG image 16 may have a P×P pixel resolution, where P>>M. Further preferably, second MCG image 16 has a consistent, higher pixel density than first MCG image 12. For example, if first MCG image 12 spans an image area of 20 cm×20 cm, then its pixel density would be M×M pixels per 400 cm$^2$, whereas the pixel density for the corresponding, same image area of second MCG image 16 would be P×P pixels per 400 cm$^2$. It is noted that if the image area of second MCG image 16 is bigger than that of first MCG image 12, then second MCG image 16 preferably maintains the same pixel density over its entire image area.

Second MCG image 16 is submitted to electric current localizer 24, which resolves the inverse problem to estimate the three-dimensional (3D) location and moment of the current source 20 that generated magnetic field as depicted in second MCG image 16. That is, electric current localizer 24 determines the 3D position and momentum of an electric current in accord with the second MCG image 16. Preferably, electric current localizer 24 evaluates electromagnetic output data as they would be observed in individual electromagnetic sensors in an x-y orientation (Bxy) assuming a single dipole and computes a dense Bxy from a dense Bz, where "B" refers to a magnetic field. Electric current localizer 24 then finds the image maximum in the intermediate MCG image, and uses this determined position information as a starting point in an iterative process for identifying a 3D position vector $\vec{p}$ and momentum vector $\vec{J}$ for the electric current.

Figure 5:
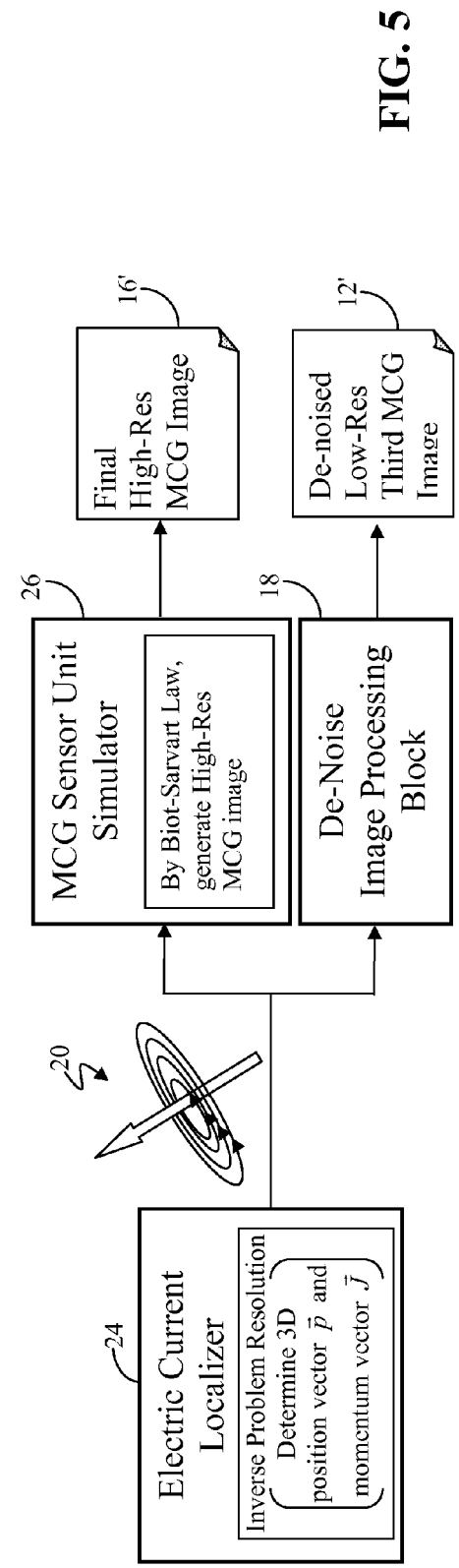
FIG. 5 illustrates two possible uses of a determined 3D position vector position vector $\vec{p}$ and momentum vector $\vec{J}$ of electric current (i.e. a current dipole).

Once 3D position vector $\vec{p}$ and momentum vector $\vec{J}$ of electric current source 20 are known, it may be used for multiple applications. For example in FIG. 5, 3D position vector $\vec{p}$ and momentum vector $\vec{J}$ may be submitted to an MCG sensor unit simulator 26, which may generate a final, and more accurate, simulated high-res MCG image 16' by use of the Biot-Sarvart law. Alternatively, the identified 3D position vector $\vec{p}$ and momentum vector $\vec{J}$ may be submitted to a de-noise image processing block 18, which may extract a simulated low-res MCG map 12' as it would be observed by hypothetical electromagnetic sensors corresponding (in position and/or capability) to physical electromagnetic sensors 13, but rendered with reduced noise.

Thus, the accuracy with which electric current localizer 24 resolves the inverse problem has a direct affect on the accuracy of a desired final objective, or simulation. Presented below is a preferred method/system for resolving the inverse problem, and thereby improve the accuracy of the 3D position vector $\vec{p}$ and momentum vector $\vec{J}$, as identified by electric current localizer 24, for example.

Before detailing the preferred method/system for resolving the inverse problem, it is beneficial to first describe in detail a preferred method/system for defining and using high-res model 14, and to describe a preliminary method for addressing the inverse problem. After describing this preliminary method of addressing the inverse problem, a detailed description of the overall preferred embodiment is presented, below The present embodiment considers the high-res MCG image restoration (i.e. generation) problem as an exemplar-based super-resolution problem. Typically, exemplar-based problems require a library of true examples (i.e. true sample images) from which to learn characteristics of such true examples. However, since it is impractical, if not impossible, to measure dense magnetic fields, it is not feasible to obtain such true examples from directly observed true measurements. Therefore, the presently preferred embodiment uses computer-generated (i.e. synthetic) high-res (training) MCG images as the library of true sample images for training purposes. That is, the present model learning algorithm is based on synthesized high-res MCG images.

The synthesized high-res MCG images that comprise the present library of sample images are preferably randomly generated based on the Biot-Savart Law. From these sample images, a linear model is constructed, preferably by use of principal component analysis (PCA). Sparse, true measurements from a physical MCG sensor unit may then be projected into the subspace of the thus-constructed linear model to estimate model coefficients and restore (i.e. create, synthesize or generate) a high-res MCG image as a model instance of the linear model. This model instance may be output from the high-res model as a high-res MCG image representation of the low resolution image/map defined by the physical MCG sensor's spare measurements.

Figure 6:
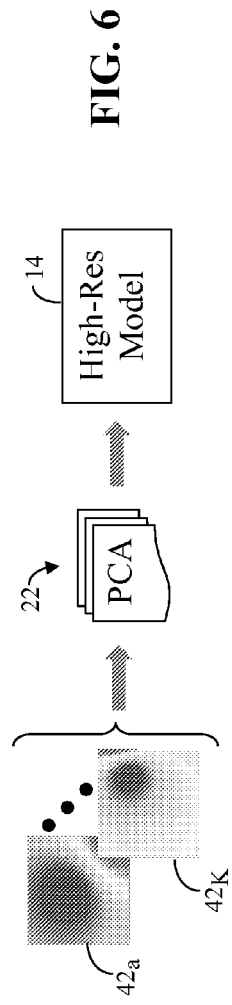
FIG. 6 shows a simplified summary of a preferred method of creating a high-res model by principal component analysis (PCA).

To recapitulate with reference to FIG. 6, a plurality of high-resolution, training images $42_a$ to $42_k$ are submitted to principal component analysis (PCA), block 22, to define high-res model 14. As is explained above, an immediate problem that needs resolving is how to obtain the multitude of high-resolution training images $42_a$-$42_k$ since such high resolution images/maps are not physically obtainable given the current state of the art of physical MCG sensor units, as depicted in FIG. 3, for example. A presently preferred solution to this problem is to simulate the needed, high-resolution training images $42_a$ to $42_k$.

Figure 7:
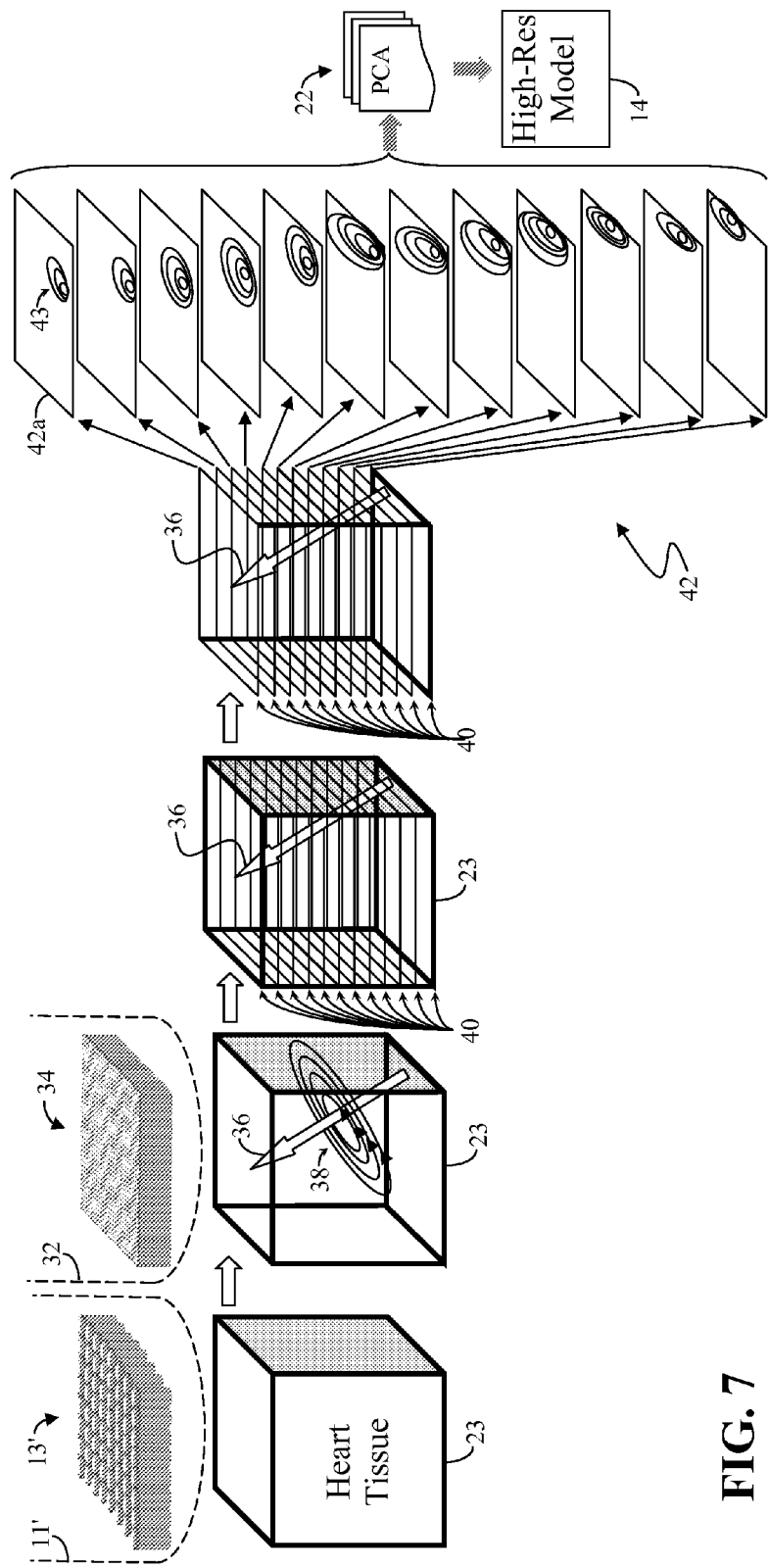
FIG. 7 is a more detailed summary of the method of FIG. 6.

With reference to FIG. 7, where all elements similar to those of FIGS. 3 and 6 have similar reference characters and are describe above, the basic ideal is to simulate heart 19 (shown in FIG. 3) as heart tissue block 23, and then to simulate a plurality of current impulses 36 within heart tissue block 23. Since the physical properties of heart tissue 23 (and any other intervening tissues/mediums between heart 19 and physical MCG sensor unit 11) are known, the propagation of a magnetic field through heart tissue block 23 as generated by current impulses 36 can be simulated. The size of heart tissue block 23 may be of comparable size as heart 19 (or of similar volume as an average human heart).

In FIG. 7, a simulated MCG sensor unit 11' similar to physical MCG sensor unit 11 of FIG. 3 is shown over heart tissue volume (i.e. block) 23. Simulated MCG sensor unit 11' could house a similar number of simulated electromagnetic sensors 13' as physical electromagnetic sensors 13 of FIG. 3. In this case, simulated MCG sensor unit 11' would be a low resolution MCG sensor unit, like that of FIG. 3. However, since an objective of the present case is to enhance the measurement readings from a physical MCG sensor unit, and since one is free to define simulated MCG sensor unit 13' to have any desired features, it is preferred that low resolution simulated MCG sensor unit 11' be replaced with a hypothetical, high resolution, simulated MCG sensor unit 32.

Hypothetical high-res MCG sensor unit 32 would have a similar resolution as the desired high-res training MCG images $42_a$-$42_k$, and thus would house a larger array 34 of simulated electromagnetic sensors, one per pixel of a desired high-res MCG image. Random, current impulse 36 could now be defined within heart tissue volume 23, and its resultant magnetic field 38 generated by use of the Biot-Savart Law. High-res MCG sensor unit 32 would now make high resolution readings (i.e. generate high-res, training MCG images) of the magnetic field 38 at various depths within heart tissue volume 23.

For practical reasons, it is preferred to generate high-res training MCG images at a predefined, limited number of depths, or layers 40 within heart tissue volume 23. The individual layers 40 can then be extracted from heart tissue volume 23, and separated to create individual high-res training MCG images 42 for each depth level. It is to be understood that a multitude of random current impulses would be defined, their magnetic fields generated, and resultant level images created. In one embodiment, 1000 random current impulses are defined, and 1000 sample images are created per depth level. These simulated high-res, training MCG images 42 are then used to construct PCA-based, high-res MCG image model 14.

In this embodiment, the area covered by hypothetical, simulated high-res MCG sensor unit 32 may be the same as the area covered by simulated low-res MCG sensor unit 11', which in turn may match that of physical low-res MCG sensor unit 11. A more detailed discussion of the construction of high-res model 14 is as follows.

The present embodiment utilizes various computing devices (or data processing devices) to learn (i.e. create) a linear model from a set of synthesized high-res MCG images generated by random electric impulse currents. Sparse data (i.e. a low resolution image) received from an MCG sensor unit is then projected onto the linear model, and a high resolution image representation of the low resolution image is created there from.

Figure 8:
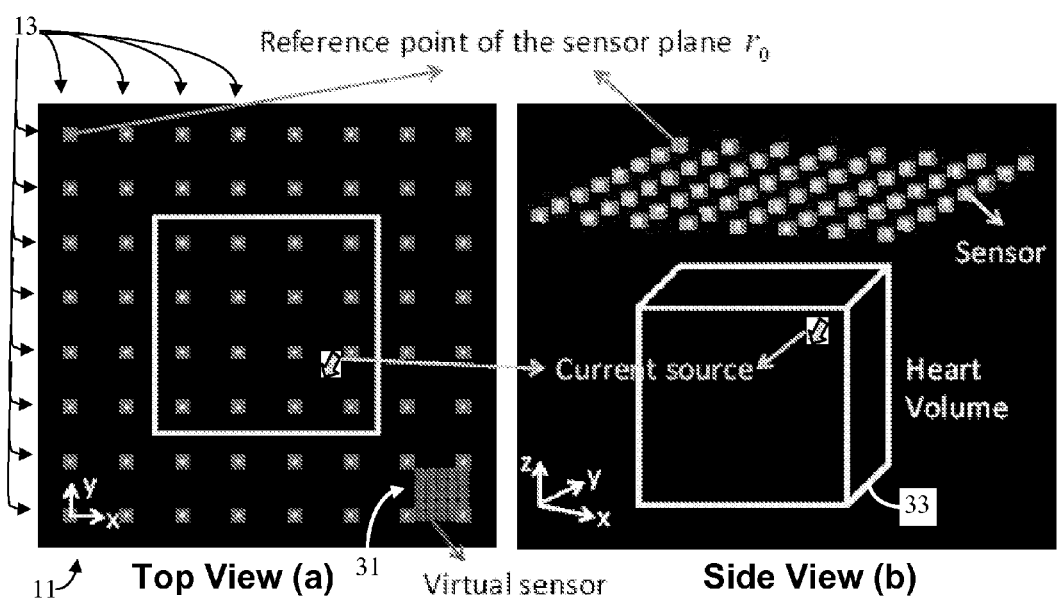
FIG. 8 illustrates the top view and side view of 3D spatial heart volume in a simulation setup.

With reference to FIG. 8, Top View (a) illustrates a top-view of a 2D sensor array (or sensor plane) in relationship to a side-view, 3D spatial heart volume 33 [Side View (b)] in a simulation setup. In the present example, Top View (a) illustrates a top view of an MCG sensor unit (such as MCG sensor unit 11 of FIG. 3) with 64 physical sensors 13 (such as electromagnetic (SQUID) sensors 13) arranged in an 8×8 sensor array. In the present embodiment, however, a set of four virtual sensors 31 are inserted in-line between adjacent real, physical sensors 13 in the x- and y-directions. Additionally, the square area defined by four corner physical sensors 13 and their four aligned sets of virtual sensors 31 is filled with a 4×4 array of additional virtual sensors 31. Thus, the present embodiment adds 1232 virtual sensors 31 to the 64 physical sensors 13 for a total of 1296 simulated sensors. This is equivalent to a 36×36 sensor array, and constitutes the basis for one implementation of the present, simulated, high-res, training images. Assigning one image pixel per sensor, the present implementation thus provides for P×P (P>8) pixels in a high-res MCG image. Preferably, the sensor plane is 5 cm to 10 cm above heart volume bounding box 33, which in the present case is 10 cm³ (i.e. 10 cm×10 cm×10 cm). In this example, the pixel density in each high-res MCG image would be (1296 pixels)/(100 cm²), or about 13 pixels per square centimeter (i.e. the high-res image has more than 20 times the resolution of the low-res image). The electric current is represented by a vector located at a 3D point.

It is to be understood that the number of virtual sensors, and thus the value of P is a design choice. FIGS. 10A to 10C show various equations (Eq. 1 to Eq. 12) to facilitate the following discussion.

Given a single electric current, a resultant magnetic field at each sensor can be computed based on the Biot-Savart Law, equation Eq. 1, where $\vec{J}(\vec{p})$ is the moment of the electric current including its magnitude and orientation. In this case, $\vec{p}$ is the 3-dimensional (i.e. 3D) position vector of the electric current. Note that this representation of electric current is an approximation by assuming the size (or magnitude) of the current is zero. One can consider that the volume (size, or density) information is included in the moment vector $\vec{J}$. $B(\vec{r}_m)$ is the magnetic vector measured by the $m_{th}$ sensor at position $\vec{r}_m = \vec{r}_o + \vec{\delta}_m$, where $r_o$ is the reference point of the sensor plane and δm indicates the offset of the $m_{th}$ sensor with respect to $r_o$. As it would be understood, $\mu_o$ is the magnetic constant.

As it is known in the art, typical MCG systems are capable of measuring only the z component of $\vec{B}$. Thus, to simulate MCG system measurements, one needs to determine the z components of a simulated $\vec{B}$.

From Eq. 1 one may compute $B_z$ (the z component of $\vec{B}$) by means of equation Eq. 2, where $J^1$, $J^2$, $J^3$ represent the three components of the current moment vector $\vec{J}$; $x_p$, $y_p$, $z_p$ represent the three components of the current position vector $\vec{p}$; and $r_m^1$, $r_m^2$, $r_m^3$ represent the three components of the sensor position vector $\vec{r}_m$.

As explained above, a set of high-res P×P MCG images (where P>>M, for example, P may be four times greater than M) are synthesized in a training step. To generate each high-res P×P MCG image, a single electric current with both random moment and random 3D position is defined. The resultant high-res P×P MCG image is computed based on Eq. 2.

Each synthesized high-res MCG image is generated by a single electric current with both random moment and 3D position. Since the magnetic field generated by the heart is very weak ($10^{-12}$ to $10^{-10}$ Tesla), the high-res MCG image is preferably normalized to 0~255 and displayed using a JET color map. In this manner, K high-res MCG training images are generated, i.e. synthesized. All the image vectors are centralized (the mean vector is denoted by μ), and they are stacked into a matrix A. Matrix A thus consists of K columns of P×P vectors. PCA is applied to extract the eigenvectors of matrix A, and thus define an eigenmatrix Σ.

A received sparse M×M MCG image, as measured by an MCG sensor unit, defines a vector g. To restore (i.e. create or define) a high-res MCG image representation of the given sparse M×M measurements (i.e. vector g), one first extracts from the eigenmatrix Σ the rows corresponding to the rows defined by the M×M measurements to form a sub-eigenmatrix Σg. Similarly, vector g's corresponding elements from mean vector μ form a sub-mean vector $\mu_g$. Vector g is then projected to sub-eigenmatrix Σg, and model coefficients $c_g$ are calculated as $c_g = \Sigma_g^+(g_j - \mu_g)$, where $\Sigma_g^+$ is the pseudo inverse of Σg. Finally the original eigenmatrix Σ along with estimated coefficients $c_g$ are used to construct a high-res MCG image vector h, as $h = \Sigma \cdot c_g + \mu$, where h is a P×P vector.

Figure 9:
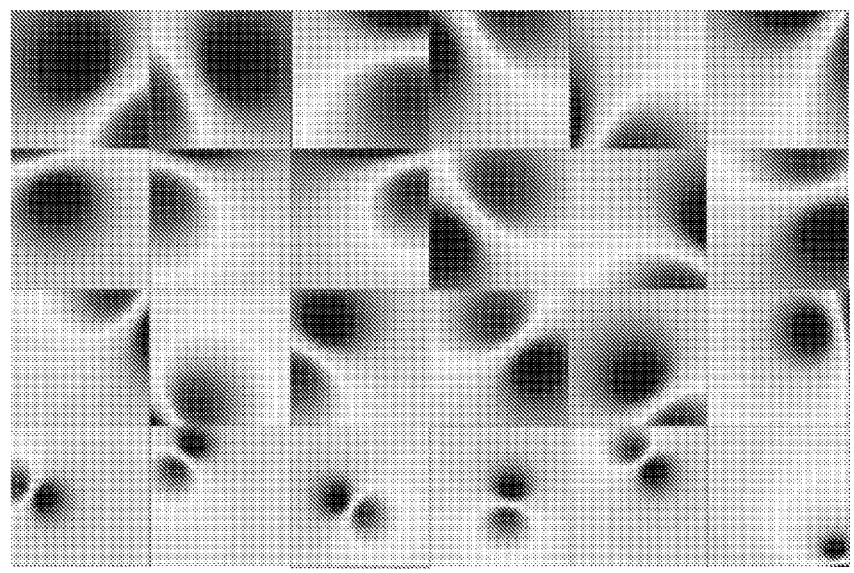
FIG. 9 shows some examples of synthesized training images.

Some examples of synthesized training images are shown in FIG. 9. Four rows of different MCG images (i.e. four 2D MCG images) generated at four respective depths, or layers, are shown. A big variance can be seen between the MCG images with changing depths.

Figure 11:
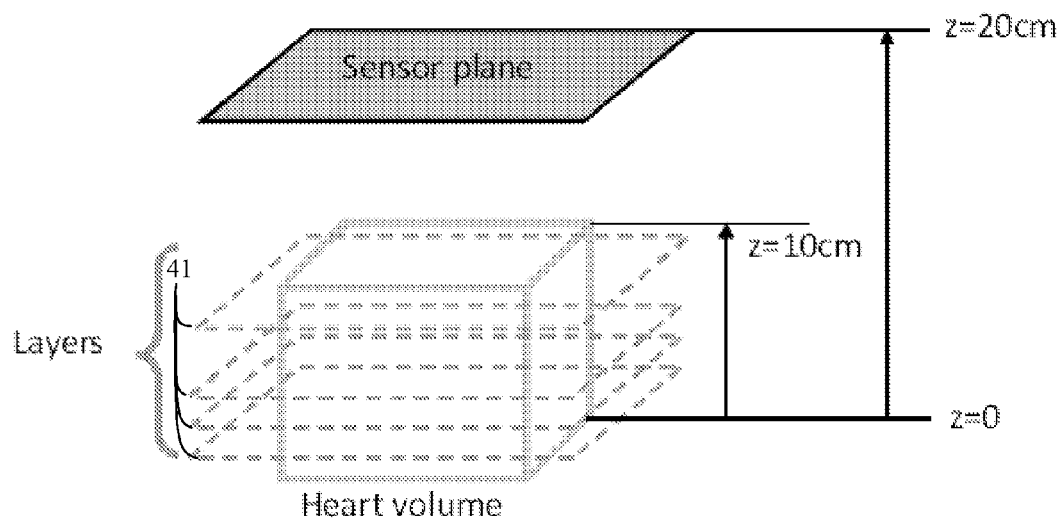
FIG. 11 illustrates depth layers in a heart volume in accord with the present invention.

An illustration of these depth layers 41 is shown in FIG. 11. In the presently embodiment, electric currents are randomly generated at different depth layers 41. It would be too exhaustive to sample every depth to select a set of depth layers. This approach assumes that $B_z$ can be approximated as a linear function of the current depth, as is explained more fully below.

In the present approach, the sensor positions $\vec{r}_m$, the 2D position ($x_p$, $y_p$), and the moment $\vec{J}$ of the electric current are fixed. $B_z$ is only affected by the depth z of the current. Thus, Eq. 2 can be simplified to Eq. 3, where $a_m$ and $b_m$ are constants but unknowns, c=20 cm is the depth of the sensor, and z is the depth of the current, which varies between 0 to 10 cm within the heart volume bounding box. Preferably, $a_m$ lies in a range from -7.5 to 7.5 cm, and $b_m$ lies in a range from 0 to 112.5 cm.

By applying Taylor expansion to Eq. 3, one obtains Eq. 4. By ignoring $O(\Delta z^3)$, one only needs to prove that $$\frac{d^2}{2dz} B_z^m(z)$$

is close to zero for any possible z and any sensor.

Figure 12:
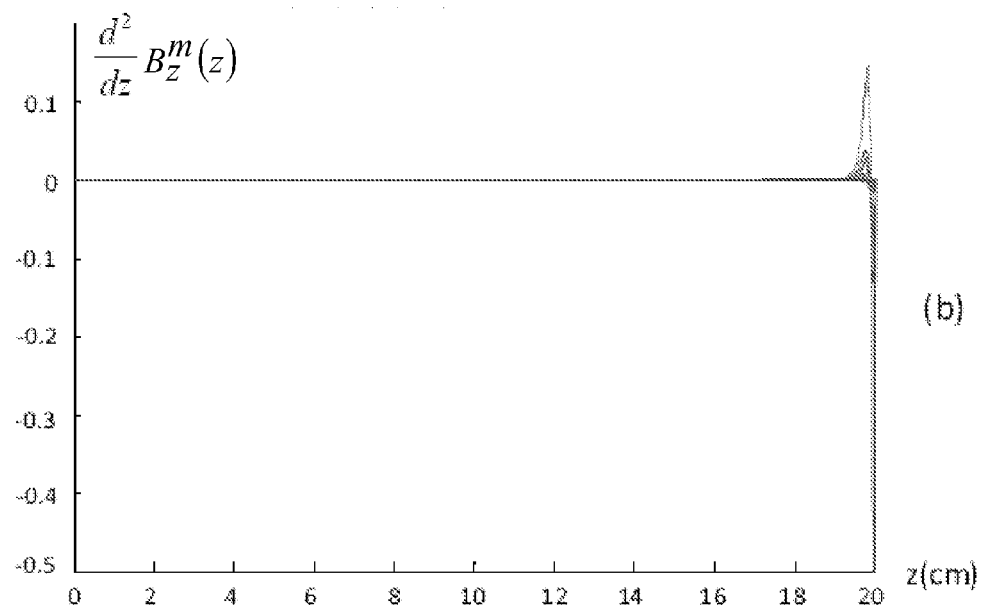
FIG. 12 is a graph of graph of $$\frac{d^2}{2dz}B_z^m(z)$$

A graph of $$\frac{d^2}{2dz} B_z^m(z)$$

versus depth, z, is shown in FIG. 12. More specifically, the graph shows $$\frac{d^2}{2dz} B_z^m(z)$$

in 64 trials with random $a_m$ and $b_m$ in each trial. As shown, $$\frac{d^2}{2dz} B_z^m(z)$$

demonstrates a very small value (close to zero) when z varies from 0 to 10 cm. Therefore, a set of depth layers may be sampled within this depth range, as is illustrated in FIG. 11.

In the present example, one thousand high resolution, training MCG image samples were generated in each of 10 evenly distributed depth layers, or levels.

The Bz view and Bxy view of the present method of creating a high-res MCG image was then compared with the prior art bicubic interpolation method, described above, as well as with the ground truth images, as is illustrated in FIG. 13. For evaluation purposes, a high-res MCG image reconstructed from the ground truth current based on the Biot-Sarvart Law is shown. To better simulate physical conditions, 5% uniformly distributed random noise was added to each simulated sensor, and the presently preferred method as well as the prior art bicubic interpolation method were then applied to the noisy sensor results. As is visually evident from the side-by-side comparison of the three images, the high-res MCG image constructed by means of the presently method more closely matches the ground truth MCG image. Thus the present method achieves a higher level of accuracy in constructing high-res MCG images than the bicubic interpolation method.

With the high-res, training MCG images thus reconstructed, the generated high-res MCG image may be analyzed to identify the location, depth, magnitude and orientation of an electric impulse current that would produce such an image.

As is explained above, true MCG images obtained from observed physical measurements are typically comprised of low-res, 2D MCG maps that do not provide enough information for directly recovering specific electric impulse current information. However, once a high-res MCG image estimation of the low-res, 2D MCG map is constructed, the 2D position of the electric current can be localized as the maximal point of the tangential components of the constructed high-res MCG image. That is, a 2D estimate of the electric current location can be obtained by analyzing the constructed high-res MCG image.

A presently preferred method for improving the localization accuracy is to solve a nonlinear optimization that reconstructs both 3D position and moment of the electric current, i.e. the inverse problem. The higher the accuracy of the estimated high-res MCG image produced by the linear model, the better the initialization for the inverse problem, which helps it converge on the global optimum more quickly. At the same time, the depth, magnitude and orientation of the electric current are also recovered. More specifically, the present method iteratively alternates between two steps (i.e. alternates between estimating a high-res MCG image using the linear model and resolving the inverse problem from the estimated high-res MCG image). The first step estimates the originating position of 3D electric impulse current, and the second step reconstructs its magnitude and orientation based on the estimated originating position. In the estimating of the originating position of 3D electric impulse current, the 2D current location estimated from the model based restoration is used as the initialization. The present method is efficient, accurate and reliable without the need of special assumptions. For the sake of simplicity, the present system/method is illustrated as applied to a single electric impulse current case only. It is to be understood, however, that extension of the present system/method/device to multiple impulse currents is straightforward.

The preferred method for generating a 2D estimate from an estimated high-res MCG image is as follows.

Given a high-res MCG image $B_z(i,j)(i=1, 2, \ldots, N; j=1, 2, \ldots, N)$, the maximal point of the tangential components $B'_{xy}(i,j)$ of $B_z(i,j)$ refers to the 2D position $(x_p, y_p)$ of the electric current. This may be seen in the second row images of FIG. 13. The tangential components of $B_z(i,j)$ may be computed using equation Eq. 5. One now is left with solving the inverse problem.

The inverse problem is to solve both 3D position $\vec{p}$ and moment $\vec{j}$ of the electric current. This approach may be better understood with reference to FIG. 14, where $\vec{r}_o$ is set as the world origin. If $\vec{p}$ is given, the inverse problem becomes a linear one. First, Eq. 1 may be rewritten as Eq. 6, where $\vec{B}^m = \vec{B}(\vec{r}_m)$, $\vec{J} = \vec{J}(\vec{p})$, and $$\vec{R}_m = \frac{\mu_O}{4\pi} \frac{(\vec{r}_m - \vec{p})}{\|\vec{r}_m - \vec{p}\|^3}.$$

Eq. 6 is then expanded to a matrix form by using a skew symmetric matrix, which results in Eq. 7 of FIG. 10B. In this case, the z component of the magnetic field can be computed as shown in Eq. 8, where $R_m^1, R_m^2$ are x,y components of $\vec{R}_m$. Given M sensors, a linear system is defined as illustrated in equation Eq. 9, where B is a measured M×1 vector, R is a M×2 position matrix that is computed from given $\vec{p}$ and $\vec{\delta}$. In the present case, J is a 2×1 unknown vector. When rank(R)≥2 (this holds for the single electric current case with 64 sensors), one can solve a least square solution for J, as illustrated in equation Eq. 10.

Note that by only measuring $B_z$ it is impossible to recover $J^3$. In fact, the magnetic field generated by the z component of the current only propagates along the horizontal direction and never reaches outside of the body. For the following computation, one sets $J^3=0$. Given an estimated current moment $\vec{J}=[J,0]$, one can update the current position $\vec{p}$.

Eq. 1 is rewritten as equation Eq. 11. One may then let $\alpha=4\pi/\mu_0$, and $\vec{\epsilon}_0 = \vec{r}_0 - \vec{p} \cdot \vec{\delta}_m$ is known for each sensor. One may then apply equation Eq. 12 to obtain $\alpha\vec{B}^m$. In Eq. 12, let $\vec{\tau}_m = \vec{J} \times \vec{\delta}_m$ and $\vec{\epsilon}_0 = (x_\epsilon, y_\epsilon, z_\epsilon)^T$. It is noted that $\vec{\tau}_m$ can be computed given $\vec{J}$. Again, the cross product is removed from Eq. 12 by using a skew-symmetric matrix. Therefor for each sensor m=1: M, one obtains a nonlinear equation in terms of $(x_\epsilon, y_\epsilon, z_\epsilon)$, as illustrated in Eq. 13. Letting $F=(f^1; f^2; \ldots; f^M)=0$, one then solves a least square solution of the nonlinear system F for $\vec{\epsilon}_0$.

Once the offset $\vec{\epsilon}_0$ is obtained, the position matrix R can be updated and J can be recomputed. These iterations are repeated until the algorithm converges. The inverse problem step converges in real time (0.5 seconds on average). Finally $\vec{p} = \vec{r}_0 - \vec{\epsilon}_0$. Since the high-res MCG image only provides an estimate for 2D current position $(x_p, y_p)$, the initial depth z and magnitude $\|\vec{J}\|$ of the electric current are given by equation Eq. 14, where d is the distance between two magnetic poles in the high-res MCG image.

Having described a preferred method/system for defining and using high-res model 14, and described a preliminary method for using a reconstructed high-res image in the solving of the inverse problem, a detailed discussion of an improved method/system for resolving the inverse problem is now presented below.

As is explained above, accurate reconstruction of an electric dipole is important to obtaining accurate results in magnetic imaging applications, and the presently preferred method/system for dipole reconstruction is based on solving the inverse problem. Furthermore, the reliability and accuracy of the preferred method/system for solving the inverse problem highly depends on the initialization and number of independent constraints or measurements. By obtaining/creating more constraints or measurements, the reliability and accuracy can be improved. The following method/system focuses on increasing the number of constraints or measurements obtained from a physical magnetic imaging system, such as an MCG system.

A first step is to synthesize a high-res image from a real-world, low-res image/map produced by a limited number of physical magnetic sensors. As is explained above, and illustratively summarized in FIGS. 6 and 7, the presently preferred method for creating a high-res model for synthesizing such high-res images is to synthesize a large number of high-res training images and apply PCA analysis. Once the high-res model is created, it may be used to synthesize, i.e. reconstruct, a high-res image from the real-world, low-res image measurements. Initialization conditions/constraints may then be extracted from the reconstructed high-res image to resolve the inverse problem.

An overview of the above-described process for resolving the inverse problem is illustrated in FIG. 15. A real-world low-res image 61 (obtained from physical measurement) is submitted to a high-res model fitting block 63, which a reconstructs a high-res image by model fitting. A current dipole is determined from the high-res image, which provides the initialization conditions for an inverse problem solver (data processing) block 65. Constraints (for example physical magnetic measurements) from the real-world, low-res image are also submitted to the inverse problem solver block 65, which outputs a (preferably 3D) estimated current source 20. That is, the original low-res image measurements are used to solve the inverse problem.

An overview of the preferred method/system for improving the accuracy of an inverse problem solver is provided with reference to the block diagram of FIG. 16 and the flow chart of FIG. 17. The basic idea is to make use of an inverse problem solver block multiple times, each time providing more accurate initialization conditions and constraints. For illustration purposes, the examples of FIGS. 16 and 17 illustrate using an inverse problem solver block two times, and a process for improving the initialization conditions and constrains for the second inverse problem solver block 85 as compared to those submitted to the first inverse problem solver block 73.

A preliminary step S0 is to build a high-res model from a set of randomly generated, simulated, high-res MCG images (such as described above, for example). Preferably, this is achieved by PCA analysis. The high-res model forms part of high-res model fitting block 71.

The general process begins with accessing a real-world, low-res image/map 61 obtained from physical magnetic sensors (step S1), such as those in an MCG system.

The next step S2 is to construct a high-res image representation of the real-world, low-res image 61. This maybe achieved by submitting real-world low-res image 61 to high-res model fitting block 71, which fits real-world low-res image 61 to the high-res model created in preliminary step S0 to reconstruct a high-res image.

Next, the 2D location of the current source is estimated from the reconstructed high-res image (step S3). A first set of initialization parameters (Initialization_1) are determined from the estimated 2D location of the current source (step S4). The first set of initialization parameters (Initialization_1), and a first set of constraints (Contraints_1) are submitted to inverse problem solver block 73.

In step S4, the initialization from the given estimated current source (i.e. Initialization_1) along with Constraints_1 are used to solve the inverse problem (in inverse problem solver 73). Using the Biot-Savart law, a low-res magnetic filed at a plurality of simulated sensor positions is computed, each corresponding to a physical magnetic sensor (from MCG system, for example), to produce a reconstructed low-res image, which is herein identified as estimated_source_1 (see FIG. 16).

Estimated_source_1 is passed to processing block 75, which computes low-res measurements (each having a one-to-one correspondence (by image pixel location) with the real-world physical measurements of low-res image 61). The computed low-res measurement (i.e. second low-res image/map or reconstructed low-res magnetic field) is passed to processing block 77, which then updates the computed low-res measurements taking into consideration the actual physical measurements of first low-res image 61. These process steps are descried in step S5.

In step S5, the reconstructed low-res magnetic field (i.e. the second low-res image) is compared with the original low-res measurements (i.e. first low-res image 61), and the result of the comparison is a third low-res image. That is, each calculated measurement in the second low-res image is compare with its corresponding physical measurement in the first low-res image 61, and if the difference between two corresponding measurements is bigger than a predefined threshold (of preferably $0.4e^{-13}$), the calculated value of the second low-res image is retained, otherwise it is replaced with the corresponding original measurement (from first low-res image 61). The combining of the first and second low-res images in this manner constitutes a third low-res image. In other words, the (reconstructed) second low-res image is updated to produce a third low-res image, as follows: for each sensor position in the second low-res image, if the difference between its current magnetic field value and the value of the its corresponding physical magnetic sensor in the first low-res image 61 is bigger than the predefined threshold, then its current magnetic field value is retained; else its current magnetic field value is replaced with the original physical measurement The updated reconstruction low-res image (i.e. the third low-res image) is submitted to high-res model fitting block 79, which constructs a second high-res image from the third low-res image (step S6). As before, this may be done by fitting the first low-res image to the high-res model. High-res model fitting block 19 and high-res model fitting block 71 may be part of a common data processing block, or each may be a separate data processing block.

The second high-res image is then passed to processing block 81, which again extracts measurement values, but this time extracts more measurement values than are found in first low-res image 61. Nonetheless a subset of the extracted measurements from the second high-res image maintain a one-to-one correspondence with the physical measurements (as explained above in reference to blocks 75-77 and step S5). The extracted measurement values constitute an extracted field map (or extracted image map). As is recited in step S7, the extracted field map is created by extracting more magnetic field values from the second high-res MCG than are found in the real-world low-res image 61. That is, more interpolated measurements are extracted from the second high-res MCG image than the original 64 measurements of first low-res image 61. For example, 15×15 or 36×36 measurements may be extracted; in which case the extracted field map constitutes a 15×15 image/map or a 36×36 image/map, respectively. In a one implementation, the high-res image produced by high-res fitting model fitting block 79 has a 351×351 resolution, and the block 81 extracts 351×351 measurements. Thus, the resolution of the extracted field image map is higher than the original low-res image/map 61 (obtained by real-world measurements) and may be up to the resolution as the second high-res image produced by high-res model fitting block 79.

Furthermore, in an optional implementation, this second high-res image produced by high-res model fitting block 79 may be of higher resolution than the first high-res image produced by high-res model fitting block 71. This may be achieved by using training images of higher resolution in the defining of high-res model fitting block 79 than were used in the defining of high-res model fitting block 71. In this case, the extracted field image map from block 81 may be of higher resolution than the first high-res image produced by high-res model fitting block 71.

The extracted field map is then passed to processing block 83 to further update the extracted measurements, as is described in step S9. The extracted field map is preferably updated as follows: within the extracted field map, replace the extracted values (of the above-described subset of the extracted measurements) at the sensor positions corresponding to physical magnetic sensors with their corresponding updated reconstructed low-res image values (i.e. from the second low-res image), as indicated by line 89 in FIG. 16. That is, the corresponding 64 components of the extracted measurements are replaced by the updated low-res measurements.

It is to be understood that update low-res measurement block 77 and update extracted measurement block 83 may be a part of a common image updating processing block.

The updated extracted field map constitutes a second set of constraints (i.e. Constraints_2), larger than the first set of constraints, Constraints_1. A second set of initialization parameters (Initialization_2) are determined from the second high-res image produced by high-res model fitting block 79, in a manner similar to that described above in reference to high-res model fitting block 71 (i.e. the 2D location of its current source is estimated, and it is used as initialization to solve the inverse problem). The second set of initialization parameters (Initialization_2) and the second set of constraints (i.e. Constraints_2) are passed to inverse problem solver block 85, which uses Initialization_2 and Constraints_2 to again solve the inverse problem (step S10). This produces a second estimated source (estimated_source_2) 87 that is more accurate than the first estimated source (estimated_source_1). Inverse problem solver block 85 and inverse problem solver block 73 may be part of a common data processing block, or each may be a separate data processing block.

Inverse problem solver blocks 73 and 85 may be part of a common inverse problem solver block.

A more detailed implementation of the preferred method/system of FIGS. 16 and 17 is described below.

As is explained above, High-res magnetic field images not only provide good initialization and more constraints for solving the inverse problem, but also provide more diagnostic significance. Doctors can directly "see" the electric activities in the heart from the high-res images. For the sake of simplicity, the case of a single current source is herein described, with the understanding that expansion from a single current source to multiple current sources is within the scope of those versed in the art. A high-res magnetic field image is first generated based on model learning. Since it is infeasible to obtain high-res magnetic field images from true measurements, synthesized high-res magnetic field images are used as sample training images. The training images are randomly generated based on Biot-Savart law. The algorithm constructs a linear model from the synthesized, random, sample high-res magnetic field images by applying principal component analysis (PCA). In practice, the sparse measurements obtained from an array of SQUIDs are projected into the subspace of the linear model, the model coefficients are estimated, and the high-res magnetic field image is restored (i.e. generated) as a model instance, as illustrated in image FIG. 18*b*.

A 2D sensor array and corresponding high-res magnetic field images are illustrated in FIGS. 18*a*, 18*b* and 18*c*. FIG. 18*a* shows an 8×8 sensor array on x-y plane that would produce a low-res image: each of the 64 sensors measures the z direction of the magnetic field. The $(p_x, p_y)$ coordinates represent the 2D projection of the current source $\vec{J}(\vec{p})$. In this illustration, the bounding box represents a bounded homogeneous planner volume conductor which restricted the possible position of current sources in 3D space.

FIG. 18*b* shows a high-res magnetic field image generated from a low-res image by means of the present method. Given a single current source, there will be two magnetic poles in the high-res magnetic field image. The middle point between two poles indicates the 2D projection of the current source. Rotating the vector $\vec{d}$ by 90 degrees counterclockwise yields the current direction 91.

FIG. 18*c* shows the tangential components of the high-res magnetic field image: the maximum of the image represents the 2D projection of the current source.

Good initialization for the position and magnitude of the current source can be extracted from the constructed high-res magnetic field image (FIG. 18*b*). The maximal point in the tangential image of the high-res magnetic field image (see FIG. 18*c*) indicates the 2D projection of the current source on the x-y plane. The distance between the two magnetic poles (see FIGS. 18*b* and 18*c*) gives the initial estimation of the depth of the current source. The magnitude of the current source can also be estimated by computing the maximum of the magnetic field from the constructed high-res image.

From Biot-Savart law, it can be understood that magnetic filed is a nonlinear function with respect to the position parameters of the current source, and a linear function with respect to the moment parameters of the current source. Therefore the presently preferred method utilizes a dual-update algorithm that alternates two steps iteratively, instead of involving all unknowns in a big optimization process. The first step estimates the 3D position of the current source by solving a nonlinear optimization, and the second step reconstructs its magnitude and orientation by solving a linear system. With good initialization from the restored high-res magnetic field image, the present method efficiently achieves accurate and reliable results. It is further demonstrated that high-res magnetic filed can provide more constraints to the inverse problem, which helps improve the accuracy.

The following detailed description assumes a planner sensor array consisting of M×M magnetic sensors is placed on x-y plane in 3D space. Each sensor measures the z component of the magnetic field, i.e. Bz. Under the sensor plane there is a bounded homogeneous volume conductor with a cubic shape and planer surface. The distance between the sensor plane and the upper surface of the conductor is denoted as D. The spacing between adjacent sensors is ω. This setup is similar to the typical MCG system described above. Without loss of generality, it is further assume that M=8, D=10 cm, ω=2.5 cm and the bounding box of the volume conductor is 10×10×10 cm$^3$). The entire measuring area assumed to be 17.5×17.5 cm$^2$. Given the theory of a bounded homogeneous magnetic volume conductor with planner surface, and given that a is perpendicular to the surface of the conductor (x-y plane), the value of a will not be affected by the volume current, which is an important advantage over electric recording systems. It is further assumed that the present setup is in a shielding room that eliminates the environmental noise. Therefore only measurement noise is considered, herein.

The following discussion makes use of the equations listed in FIGS. 19a and 19b. Part of the following discussion parallels the detailed discussion provided above, but for ease of explanation, some formulas provided above are repeated below, and in FIGS. 19a and 19b.

Since the present example assumes a homogeneous conductor, the dipole model is used for the current source. Furthermore, without considering the size of the current source, a point model is used to address the present algorithm. In other words, the length or size of the current source (e.g. heart muscle tissue in one real-world example) is incorporated into the moment parameter of the current source. The 3D moment vector used in the present method represents the information including magnitude, length and direction of the current source altogether.

Given a single point current source, the magnetic field measured by each sensor can be computed based on the Biot-Sarvart law, Eqn 15, where $\vec{J}(\vec{p})$ is the moment of the current source including its magnitude, length and direction. In this case, $\vec{p}$ is the 3D position vector of the point current source. In the real case it represents the geometric center of the current source with real length or size. $\vec{B}(\vec{r}_m)$ is the magnetic vector measured by the $m_{th}$ sensor at the position $\vec{r}_m$, where the world origin is located at one of the corners of the bounding box (see FIG. 18a). As it would be understood, $\mu_0$ is the magnetic constant.

Eq. 1 can be rewritten as Eq. 16, where $$\vec{R} = \frac{\mu_O}{4\pi} \frac{(\vec{r}_m - \vec{p})}{\|\vec{r}_m - \vec{p}\|^3}.$$

Eq. 16 is then expanded to a matrix form by using a skew-symmetric matrix resulting in Eq. 17.

where $R_m^1$, $R_m^2$ are x,y components of $\vec{R}_m$. $J^1$, $J^2$, $J^3$ represent the three components of the current moment vector $\vec{J}(\vec{p})$. More specifically, the z component of $\vec{B}(\vec{r}_m)$, i.e. $B_z(m)$, can be obtained from Eq. 18, where $x_p$, $y_p$, $z_p$ represent the three components of the current position vector $\vec{p}$; $r_m^1$, $r_m^2$, $r_m^3$ represent the three components of the sensor position vector $\vec{r}_m$.

In order to restore, i.e. generate or synthesize, a high-res magnetic field image/map from low-res measurements, a preliminary training step is needed to generate a set of high-res P×P magnetic field images (where P>>M). Each time, a single point current source with both random moment and 3D position is generated. The magnitude of the current source is normalized to one in training and random in testing. A high-res P×P magnetic field image based on Eq. 18 is computed.

Several examples of training images are shown in FIG. 9. Basically, each high-res magnetic field training image is generated by a single point current source with both random moment and 3D position. The magnetic field generated by the simulation is very weak ($10^{-12}$ to $10^{-10}$ Tesla), which applies to many real situations in brain and heart. All the images are displayed using a JET color map instead of using the real value. By this means, K high-res training images are generated. The images from different rows are generated from different depths (the distance of the current source in z direction).

All the image vectors are centralized (the mean vector is denoted by μ) and stacked into a matrix A. Matrix A consists of K columns of vectors in the dimension of $P^2$. Principal component analysis (PCA) is applied to extract eigenvectors of A.

To restore a high-res magnetic field image given a sparse M×M measurement which forms a vector g, the corresponding rows are first extracted from the eigenmatrix Σ to form a sub-eigenmatrix $\Sigma_g$. One then projects vector g into sub-eigenmatrix $\Sigma_g$ and calculates the model coefficients, i.e. $c_g = \Sigma_g^+(g_j - \mu_g)$, where $\Sigma_g^+$ is the pseudo inverse of $\Sigma_g$. Finally, estimated coefficients $c_g$ and the original eigenmatrix Σ are used to reconstruct (i.e. generate, estimate, or synthesize) the high-res magnetic field image vector $h = \Sigma \cdot c_g + \mu$, where h is a vector in the dimension of $P^2$. Note that only the first V modes are selected, where V<=64, otherwise there is no unique solution to the coefficients.

High-res magnetic filed images from different rows of FIG. 9 are generated in different depths (the distance of the current source in z direction). A big variance between the images can be seen as the depth changes. It is too exhaustive to sample every depth. Additionally, the selection of a set of depth layers depends on the fact that a can be approximated as a linear function of the current depth. This is proved as below. By fixing the sensor positions $\vec{r}_m$, 2D position $(x_p, y_p)$ and moment $\vec{J}$ (assuming a unit vector) of the current source. $B_z$ is a function of the current source depth z. Eq. 18 can be simplified to Eq. 19, where $$a_m = -J^2(r_m^1 - x_p) + J^1(r_m^2 - y_p),\ b_m = (r_m^1 - x_p)^2 + (r_m^2 - y_p)^2,$$

$$c = r_m^3 = 10 \text{ cm},\ z = z_p \in (10, 0) \text{cm}.$$

Taylor expansion is then applied to Eq. 19, resulting in Eq. 20. By ignoring $O(\delta)z^3$, one only needs to prove that $$\frac{d^2}{dz}B_z^m(z)$$

is close to zero or much smaller than $B_z^m(z)$. Applying the second derivative to $B_z^m(z)$ results in Eq. 21. Dividing Eq. 21 by Eq. 19 results in Eq. 22.

FIGS. 20a and 20b illustrate the spatial configuration of the sensor plane and bounding box of the present example, where 20a illustrates the top view and FIG. 20b illustrates a side view. The sensor plane covers 17.5×17.5 cm² and the bounding box covers 10×10×10 cm³. The sensor plane is 10 cm above the bounding box. From FIGS. 20a and 20b, it is evident that $b_m \in [0, 378]$cm, $(c-z)^2 \in [100, 400]$cm. Since κ is monotonically decreasing with respect to $b_m$, and when $b_m = 0$ cm, κ is monotonically decreasing with respect to $(c-z)^2$, $\max(\kappa) = \kappa(b_m = 0, (c-z)^2 = 100) = 0.1$. That is, $$\frac{d^2 B_z^m(z)}{dz^2}$$

is 10% of $B_z^m(z)$, and can therefore be ignored, and $B_z^m(z)$ may be considered to be linear. In experiments, 1000 samples were generated in each of 10 evenly distributed depth layers.

For comparison purposes, FIG. 21 shows low-res measurements, i.e. a low-res image (first column), a high-res magnetic field image restored/created by prior art method Bicubic interpolation (second column), a high res-magnetic field image generated the present method (third column), and a ground truth high-res image computed from the true current source ($\vec{J}_g, \vec{p}_g$) based on the Biot-Sarvart law (fourth column). To better simulate real-world conditions, 5% uniformly distributed random noise is added to each sensor measurement. The top row (labeled B) shows the low-res and high-res magnetic field images $B_z(i, j)$; the bottom row (labeled $B_{xy}$) shows the low-res and high-res tangential images $B_{xy}(i, j)$ of $B_z(i, j)$. The results show that the method of the present invention restores more accurate high-res magnetic field images.

The following discusses in more detail the estimation of the current source. To estimate the current source, the inverse problem has to be solved, which requires good initialization. As is mentioned above, good initialization can be obtained by analyzing a high-res magnetic field image. Furthermore, the inverse problem is herein solved in an alternative way which reduces the computational complexity and provides for fast and correct convergence.

Given a high-res magnetic field image $B_z(i, j)(i=1, 2, \ldots, N, j=1, 2, \ldots, N)$, the maximal point of the tangential components $(B'_{xy}(i, j))$ of $B_z(i, j)$ (see the second row of FIG. 21) indicates the 2D projection $(x_p, y_p)$ of the current source on the x-y plane. The tangential image of $B_z(i, j)$ is computed using the following equation Eq. 23. The initial z position and magnitude $\|\vec{J}\|$ of the current source are given by the two equation collectively labeled Eq. 24, where d is the distance between two magnetic dipoles in the high-res magnetic field image (see FIG. 18b).

The following describes the solving of the inverse problem. Since $B_z(m)$ is a linear function of the current moment $\vec{J}$ but nonlinear function of the current position $\vec{P}$, a dual-update algorithm/process/method to alternatively solve $\vec{J}$ and $\vec{P}$ in an iterative way was developed.

Given $M^2$ sensors, Eq. 18 is stacked to form a linear system, as shown in Eq. 25, where B is a measured $M^2 \times 1$ vector, R is a M×2 position matrix which is a function of position vector $\vec{p}$ and $\vec{r}_m$. J is a 2×1 unknown vector. When rank(R)≥2 (this holds for the single current source with 64 sensors), and given the initialization of $\vec{p}$, one can solve a least square solution for J, as shown in Eq. 26.

Note that by only measuring $B_z$ it is impossible to recover $J^3$. In fact, the magnetic field generated by the z component of the current only propagates along the horizontal direction and never reaches outside of the vertical upper boundary. For the following computation, it is preferred to set $J^3=0$. Given an estimated current moment $\vec{J}=[J^1, J^2, 0]$, the current position $\vec{p}$ is updated by solving a nonlinear system. Eq. 18 is rewrite as Eq. 27, where $$\alpha = \frac{4\pi}{\mu_0}.$$

Let $F=(f^1; f^2; \ldots; f^{M^2})=0$. We solve a least square solution of the nonlinear system F for $\vec{p}$.

Once the position $\vec{p}$ is updated, the position matrix R and J is recomputed. These two steps are executed iteratively (i.e. repeated) until the algorithm converges. The present algorithm converges in real time (0.5 seconds, on average).

The present method/system was evaluated using both simulations and physical phantom setups. In both scenarios, the true 3D position $\vec{p}_g$, moment $\vec{J}_g$, shape and size of the current source are known. The simulation setup is as described above, particularly as illustrated in FIGS. 11 and 20. In each testing trial, a point current source with random 3D position and moment is generated within the bounding box. $B_z$ is computed at each sensor and 5%, 10% or 15% random noise is added (with a uniform or Gaussian distribution) to $B_z$. The 64 sparse measurements with noise are used to restore/generate the high-res magnetic field image in N×N resolution. 50 pixels are inserted between two adjacent real sensors, which means that the interval between adjacent pixels in the high-res magnetic field image is 0.5 mm. In this case N=50×7+1=351.

Table 1 in FIG. 22 shows the 3D localization error resulting from the presently preferred method. As we restored high-res magnetic field images, we can use more constraints for solving the inverse problem. Table 1 also shows the results from using different number of constraints: 8×8 is from the original 64 measurements; 15×15 uses (225−64) more constraints obtained (i.e. extracted) from the restored/generated $B_z$; 36×36 uses (1296−64) more constraints obtained (i.e. extracted) from the restored/generated $B_z$. As one can see, using/extracting more constraints not only enhances the reliability of the algorithm but also improves the localization accuracy. Table 3 in FIG. 24 shows the difference in direction between the estimated current moment $\vec{J}_{rec}$ and the true current moment. As one can see, the direction of the current source is very robust not only to the measurement noise, but also to the depth error. Table 2 in FIG. 23 shows the source magnitude estimation error. Since the current magnitude is very weak, the relative error is computed. All the results are averaged from 150 trials.

FIG. 25 shows a comparison of the low-res magnetic image provided by low-res measurements (first column), the high-res magnetic field images restored by the linear model (i.e. the high-res model fitting of FIG. 15, for example) (second column), the high-res magnetic field computed given the reconstructed current ($\vec{J}_{rec}, \vec{p}_{rec}$) obtained by the presently preferred method (as illustrated in FIG. 16, for example) (third column), and the high-res magnetic field computed given the true current source ($\vec{J}_g, \vec{p}_g$) (fourth column). 5% uniformly distributed random noise is added to each sensor measurement. The top row in FIG. 25 shows the low-res or high-res magnetic field image $B_z(i, j)$, and the bottom row shows the low-res or high-res tangential image $B_{xy}(i, j)$ of $B_z(i, j)$. As one can see, the reconstructed high-res $B_z$ obtained the presently preferred method is closer to the ground truth.

In real-world cases, a current source has a shape and size that is more like a voxel (with a 3D cubic shape) rather than a point. Different sizes of voxel currents were simulated by generating a set of point currents sharing the same direction and magnitude, within a 3D grid by a 0.5 mm interval.

FIG. 26 shows the localization error for voxel current sources. The geometric center of the voxel current source is used as the ground truth. The results demonstrate that the presently preferred method is robust to the size of the current source, and comparable to the state of art.

With reference to FIG. 27, in a real phantom experiment, the current source has a physical shape and size. The present phantom experiment uses a 4-turn vertical circular wired coil with 0.5 cm diameter. It can be considered as a set of small line segment currents. The present method estimates the position of the geometric center of the coil. The present circular wire coil is built in the "Signal Coil" component. Above the coil there is a table that can be moved along the z direction. An 8×8 grid with marks ranging from −4 to 3 in each direction is printed on the table, at 2 cm intervals. The coil is right below the (0, 0) coordinate. A fluxgate sensor (Mag639) placed on the table is used to measure the z component of the magnetic field at each grid point. The output of the fluxgate sensor is imported to the spectrum analyzer and then converted to Tesla. By moving the fluxgate sensor to different grid points, one can obtain 64 measurements of $B_z$, at different positions. In this case, an infinite homogeneous conductor is assumed; $B_z$, will not be affected by the volume current as well. However since this setup is not shielded (i.e. is not in a magnetically shielded room), the measurements will be distorted by environmental noise in addition to the measurement noise.

Three sets of measurements were made by changing the distance between the sensor and the coil to: 5 cm, 10 cm and 15 cm, and then estimating the geometric center of the coil. Since this real phantom setup is totally unshielded, the measurement noise is big. When z=5 cm, over ¼ of sensor measurements have over 70% noise, and about ½ of sensor measurements have 30%-60% noise. For other two cases the noise ratio is in the same level. The results demonstrate that even in this noisy setup, the present method can still achieve 6 to 9 mm accuracy (see FIG. 28).

When the sensor depth increases, high-res magnetic filed images $B_z(i, j)$ and corresponding tangential images $B'_{xy}(i, j)$ change very much. However the global minimal point of $B'_{xy}(i, j)$ stays close to the ground truth robustly. This is a very encouraging result compared to the state of art using a shielded room.

It is noted that the best accuracy is achieved when z=5 cm, although the average measurement error is bigger than other two cases. One possible reason is that the local measurements closer to the coil are more accuracy.

The method is not a typical non-linear least-square solution, because such a solution does not work well in the present case. The present exemplary implementation has only up to 64 magnetic measurements from a very weak source under a highly non-linear formulation, with unknown 3D location and moment to recover. The standard solution often suffers from un-desired local optima without good initialization, especially on the source location.

Two steps are proposed. In the first step, the presently preferred method restores the high-res magnetic field image from which the 3D location of the source can be estimated accurately. This provides good initialization that is critical to the next step of non-linear optimization. Furthermore, the restored high-res magnetic field image supplies far more inputs to the optimization than the original low-res measurements and thus enhance the reliability. Second, alternatively solving for the source moment and location is proposed, instead of involving all unknowns in a big optimization process, as would be the traditional manner. This further ensures a fast and accurate convergence.

The resolution of the high-res magnetic field image can affect localization accuracy. When the resolution is decreased by changing N from 351 to 141, i.e. 20 instead of 50 pixels being inserted between adjacent real sensors, the localization error increases by 150%. On the other hand, when more than 50 pixels are inserted, the accuracy does not change much.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A system for constructing a current dipole, comprising:

a sensor unit including a plurality of electromagnetic sensors producing a sparse measurement output of data values in a direction normal to the electromagnetic sensors, said sparse measurement output constituting a first low-resolution image having a first resolution;

a high resolution image synthesizer for receiving said first low resolution image and producing a first high resolution image, said first high resolution image being a higher resolution representation of said first low resolution image;

a first inverse problem solver data processing block for receiving said first high resolution image and said first low resolution image and calculating a three-dimensional (3D) location and moment of the current source represented by the first high resolution image given the constraints of said first low-resolution image;

a low resolution image generator receiving the calculating 3D location and moment of the current source from the first inverse problem solver data processing block, and computing an intermediate low-res image having plurality of data point positions, each corresponding to one of said sparse measurements of said plurality of electromagnetic sensors as indicated in said first low resolution image;

a first image updating processing block receiving said intermediate low-res image and comparing it to said first low resolution image, wherein for each data point position in the intermediate low-res image, IF the difference between its current data value and the data value of the its corresponding sparse measurement from the first low resolution image is bigger than a predefined threshold, THEN retaining its current data value, ELSE replacing its current data value with its corresponding sparse measurement from the first low resolution image, the result being an updated intermediate low-res image;

a second high resolution image synthesizer for receiving said updated intermediate low-res image and producing a second high resolution image, said second high resolution image being a higher resolution representation of said updated intermediate low-res image;

a data extracting processing block for extracting data points from said second high resolution image, the extracted data points constituting an extracted field image of higher resolution than said first low-res image, said extracted field image including a subset of the extracted data values, each extracted data value in said subset corresponding to one of said sparse measurements of said plurality of electromagnetic sensors as indicated in said first low resolution image;

a second image updating processing block receiving said extracted field image and replacing the subset of the extracted data values with their corresponding values in said updated intermediate low-res image, the result being an updated extracted field image; and a second inverse problem solver data processing block receiving said second high resolution image and updated extracted field image and calculating a second 3D location and moment of the current source represented by the second high resolution image given the constraints of said updated extracted field image, said current dipole being defined by said second 3D location and moment.

2. The system of claim 1, wherein the data values in the produced sparse measurement output are magnetic data values.

3. The system of claim 1, wherein said intermediate low-resolution image being of equal resolution as said first low-resolution image and having a one-to-one data point correspondence with said first low-resolution image.

4. The system of claim 1, wherein said intermediate low-res image computed by the low resolution image generator is a magnetic field intermediate low-res image.

5. The system of claim 1, wherein said predefined threshold is $0.4e^{-3}$.

6. The system of claim 1, wherein said first and second high resolution image synthesizers are part of a common high resolution image synthesizing data processing block.

7. The system of claim 1, wherein the field image extracted by the data extracting processing block is a magnetic field image.

8. The system of claim 1, wherein the field image extracted by the data extracting processing block is of comparable resolution as said second high resolution image.

9. The system of claim 1, wherein said first and second image updating processing blocks are part of a common image updating processing block.

10. The system of claim 1, wherein said first and second inverse problem solver data processing blocks are part of a common inverse problem solver data processing block.

11. The system of claim 1, wherein said system is a magnetocardiogram (MCG) system having an M×M array of said electromagnetic sensors.

12. The system of claim 1, wherein said system is magnetoencephalograph (MEG) system.

13. A method of constructing a current dipole from a real-world low-resolution (low-res) image obtained from physical magnetic sensors, comprising:
   constructing a first high resolution (high-res) image representation of the real-world low-res image, said first high-res image being of higher resolution than said real-world low-res image;
   estimating a first 2 dimensional (2D) location of a first estimated current source represented by the first high-res image;
   using the first estimated current source to initialize the inverse problem, and using the Biot-Savart law along with constraints from said real-world low-res image, computing a low-res magnetic field at a plurality of simulated sensor positions, each corresponding to one of said physical magnetic sensors, to produce a reconstructed intermediate low-res image;
   updating the reconstructed intermediate low-res image as follows, for each sensor position in the reconstructed intermediate low-res image, IF the difference between its current magnetic field value and the value of the its corresponding physical magnetic sensor as determine from the real-world low-res image is bigger than a predefined threshold, THEN retaining its current magnetic field value; ELSE replacing its current magnetic field value with the original corresponding value from the real-world low-res image, the result being an updated reconstructed intermediate low-res image;
   constructing a second high-res image representation of the updated reconstructed intermediate low-res image; second high resolution image being a higher resolution representation of said reconstructed intermediate low-res image;
   creating an extracted field map by extracting magnetic field values from the second high-res image, said extracted field map being of higher resolution than said real-world low-res image, said extracted field map including a subset of the extracted data values of equal resolution as said reconstructed intermediate low-res image, each extracted data value in said subset having a one-to-one correspondence with a data value in said reconstructed intermediate low-res image;
   within the extracted field map, replacing each extracted data value in said subset with its corresponding data value in said reconstructed intermediate low-res image, the result being an updated extracted field map;
   estimating a second 2D location of a second estimated current source represented by the second high-res image;
   using the second estimated current source to initialize the inverse problem and the updated extracted field map as constraints to the inverse problem, solve the inverse problem to define said current dipole.

14. The method of claim 13, wherein said first high-res image is constructed by fitting said real-world low-res image to a high-res model.

15. The method of claim 14, said high-res model is built by PCA analysis of a set of randomly generated, simulated, high-res magnetic images with known current sources.

16. The method of claim 14, wherein said second high-res image is constructed by fitting updated reconstructed low-res image to said high-res model.

17. The method of claim 13, wherein said extracted field map is of comparable resolution as said second high-res image.

18. The method of claim 17, wherein said extracted field map and said second high-res image both are 36×36 image maps.

19. A magnetoencephalograph (MEG) system implementing the method of claim 13.

20. A magnetocardiogram (MCG) implementing the method of claim 13.

* * * * *